US011420980B2

(12) United States Patent
Yoshida et al.

(10) Patent No.: US 11,420,980 B2
(45) Date of Patent: Aug. 23, 2022

(54) SALT OF PENTACYCLIC COMPOUND AND CRYSTAL THEREOF

(71) Applicant: Eisai R&D Management Co., Ltd., Tokyo (JP)

(72) Inventors: Kenshi Yoshida, Tsukuba (JP); Yoshiaki Ohashi, Tsukuba (JP); Tamaki Hoshikawa, Tsukuba (JP); Nobuaki Sato, Tsukuba (JP); Ikuo Kushida, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 17/021,544

(22) Filed: Sep. 15, 2020

(65) Prior Publication Data
US 2021/0024541 A1 Jan. 28, 2021

Related U.S. Application Data

(63) Continuation of application No. PCT/JP2020/008889, filed on Mar. 3, 2020.

(30) Foreign Application Priority Data

Mar. 5, 2019 (JP) .............................. JP2019-039349

(51) Int. Cl.
*C07D 495/22* (2006.01)
*A61P 25/28* (2006.01)
*A61P 25/00* (2006.01)
*A61P 25/16* (2006.01)

(52) U.S. Cl.
CPC ............ *C07D 495/22* (2013.01); *A61P 25/00* (2018.01); *A61P 25/16* (2018.01); *A61P 25/28* (2018.01); *C07B 2200/13* (2013.01)

(58) Field of Classification Search
CPC combination set(s) only.
See application file for complete search history.

(56) References Cited

U.S. PATENT DOCUMENTS

| | | | |
|---|---|---|---|
| 4,187,306 | A | 2/1980 | Mayer et al. |
| 5,621,100 | A | 4/1997 | Lewis et al. |
| 5,756,494 | A | 5/1998 | Lewis et al. |
| 5,859,016 | A | 1/1999 | Suh et al. |
| 2019/0071452 | A1 | 3/2019 | Ohashi et al. |
| 2020/0283452 | A1 | 9/2020 | Ohashi et al. |

FOREIGN PATENT DOCUMENTS

| | | |
|---|---|---|
| CL | 200400348 | 1/2005 |
| CL | 200400352 | 5/2005 |
| CN | 1054600 | 9/1991 |
| CN | 101084220 | 12/2007 |
| CO | NC2021010512 | 10/2021 |
| DE | 258234 | 7/1988 |
| EP | 0441517 | 8/1981 |
| JP | S54-024896 | 2/1979 |
| JP | H9-118621 | 5/1997 |
| RU | 2117670 | 8/1998 |
| RU | 2229299 | 5/2004 |
| WO | WO 2004/033666 | 4/2004 |
| WO | WO 2019/049869 | 3/2019 |
| WO | WO 2020/179780 | 9/2020 |

OTHER PUBLICATIONS

US 10,239,899 B2, 03/2019, Ohashi et al. (withdrawn)
Chen (Pharmaceutical Crystallization, Cryst. Growth Des. 2011, 11, 887-895).*
Office Action in Israeli Patent Application No. 272652, dated Nov. 19, 2020, 5 pages (with English Translation).
Search Report in European Patent Application No. 18853415.0, dated Dec. 7, 2020, 5 pages.
Submission Document in Colombian Patent Application No. NC2020/0001471, dated Oct. 6, 2020, 11 pages (with English Translation).
Submission Document in Egyptian Patent Application No. PCT292/2020, dated Dec. 29, 2020, 7 pages (with English Translation).
Submission Document in Peruvian Patent Application No. 000228-2020/DIN, dated Dec. 9, 2020, 8 pages (with English Translation).
Submission Document in South African Patent Application No. 2020/00970, dated Dec. 8, 2020, 6 pages.
Allen et al., "Abundant tan filaments and nonapoptotic neurodegeneration in transgenic mice expressing human P301S tan protein," The Journal of Neuroscience, 2002, 21:9340-9351.
Dautan et al., "A major external source of cholinergic innervation of the striatum and nucleus accumbens originates in the brainstem," The Journal of Neuroscience, 2014, 34(13):4509-4518.
Decker, "Novel inhibitors of acetyl- and butyrylcholinesterase derived from the alkaloids dehydroevodiamine and rutaecarpine," European Journal of Medicinal Chemistry, 2005, 40(3):305-313, ISSN 0223-5234.
Everitt et al., "Central cholinergic systems and cognition," Annu. Rev. Psychol,, 1997 48:649-684.
Fischer et al., "Progressive decline in spatial learning and integrity of forebrain cholinergic neurons in rats during aging," Neurobiology of Aging, 1992, 13:9-23.
Gilmor et al., "Coordinate expression of the vesicular acetylcholine transporter and choline acetyltransferase following septohippocampal pathway lesions," Journal of Neurochemistry, 1998, 71:2411-2420.

(Continued)

*Primary Examiner* — Kathrien A Cruz
(74) *Attorney, Agent, or Firm* — Fish & Richardson P.C.

(57) ABSTRACT

Salts of the compound represented by formula (I) or crystals thereof have a potential use as drug substances for pharmaceuticals.

11 Claims, 19 Drawing Sheets

(56) References Cited

OTHER PUBLICATIONS

Gómez-Isla et al., "Neuronal loss correlates with but exceeds neurofibrillary tangles in Alzheimer's disease," American Neurological Association, 1997, 41:17-24.
Gu et al., "Recombinant human NGF-loaded microspheres promote survival of basal forebrain cholinergic neurons and improve memory impairments of spatial learning in the rat model of Alzheimer's disease with fimbria-fornix lesion," Neuroscience Letters, 2009, 453:204-209.
Gulledge et al., "Cholinergic inhibition of neocortical pyramidal neurons," J. Neurosci., 2005, 25:10308-10320.
Hemdan et al., "Uses of 1-(3-Cyano-4,5,6,7-tetrahydrobenzo[b]-thiophen-2-yl)-3-dodecanoylthiourea as a Building Block in the Synthesis of Fused Pyrimidine and Thiazine Systems," Chemical and Pharmaceutical Bulletin, 2015, 63:450-456.
Hoffmann et al., "Impaired plasticity of cortical dendritic spines in P301S tan transgenic mice," Acta. Neuropathol, Communications, 2013, 1:82.
Huang et al., "A simple heterocyclic fusion reaction and its application for expeditious syntheses of rutaecarpine and its analogs," Tetrahedron Letters, 2014, 55(26):3607-3609.
International Preliminary Report on Patentability in International Patent Application No. PCT/JP2018/032797, dated Mar. 19, 2020, 6 pages.
International Search Report in International Application No. PCT/JP2018/032797, dated Dec. 4, 2018, 12 pages (with English Translation).
International Search Report in International Application No. PCT/JP2020/008881, dated Jun. 9, 2020, 16 pages (with English Translation).
International Search Report in International Application No. PCT/JP2020/008889, dated Jun. 9, 2020, 2 pages.
Lapchak et al., "Effect of recombinant human nerve growth factor on presynaptic cholinergic function in rat hippocampal slices following partial septohippocampal lesions: measures of [$^3$H]acetylcholine synthesis, [$^3$H]acetylcholine release and choline acetyltransferase activity," Neuroscience, 1991, 42(3):639-649.
Leanza et al., "Selective immunolesioning of the basal forebrain cholinergic system disrupts short-term memoiy in rats," European Journal of Neuroscience, 1996, 8:1535-1544.
Leanza et al., "Selective lesioning of the basal forebrain cholinergic system by intraventricular 192 IgG-saporin: behavioural, biochemical and stereological studies in the rat," European Journal of Neurosceience, 1995, 7:329-343.
Lee et al., "Neurodegenerative tauopathies," Annu. Rev. Neurosci., 2001, 24:1121-1159.
Lowe et al., "Effects of a novel mGlu$_2$⅔ receptor agonist prodrug, LY2140023 monohydrate, on central monoamine turnover as determined in human and rat cerebrospinal fluid," Psychopharmacology, 2012, 219:959-970.
Mori et al., "Donepezil for dementia with Lewy bodies: a randomized, placebo-controlled trial," Ann. Neurol., 2012, 72:41-52.
Mufson et al., "Cholinergic system during the progression of Alzheimer's disease: therapeutic implication," Expert Rev. Neurother., 2008, 8:1703-1718.
Mufson et al., "Human cholinergic basal forebrain: chemoanatomy and neurologic dysfunction," Journal of Chemical Neuroanatomy, 2003, 26:233-242.
Notice of Allowance in Japanese Patent Application No. P2019-516726, dated Jul. 9, 2019, 5 pages (with English Translation).
Notice of Allowance in Taiwanese Patent Application No. 107131095, dated Jun. 18, 2020, 7 pages (with English Translation).
Notice of Allowance in U.S. Appl. No. 16/122,116, dated Nov. 15, 2018, 10 pages.
Office Action in Gulf Cooperation Council Patent Application No. GC2018-35952, dated Jan. 27, 2020, 9 pages (with English Translation).
Office Action in Japanese Patent Application No. P2019-516726, dated Jun. 11, 2019, 4 pages (with English Translation).
Office Action in Pakistani Patent Application No. 146/2020, dated Oct. 2, 2020, 2 pages.
Office Action in Pakistani Patent Application No. 612/2018, dated Dec. 6, 2019, 2 pages.
Ogura et al., "Donepezil, a centrally acting acetylcholinesterase inhibitor, alleviates learning deficits in hypocholinergic models in rats," Methods Find Exp. Clin. Pharmacol., 2000, 22(2):89-95.
Onishi et al., "Early-onset cognitive deficits and axonal transport dysfunction in P301S mutant tan transgenic mice", Neuroscience Research, 2014, 80:76-85.
Pappas et al., "Choline acetyltransferase activity and cognitive domain scores of Alzheimer's patients", Neurobiology of Aging, 2000, 21: 11-17.
Perry et al., "Neocortical cholinergic activities differentiate Lewy body dementia from classical Alzheimer's disease," Clinical Neuroscience and Neuropathology, 1994, 5:747-749.
Rogers et al., "The efficacy and safety of donepezil in patients with Alzheimer's disease: results of a US Multicentre, Randomized, Double-Blind, Placebo-Controlled Trial," Dementia, 1996, 7:293-303.
Salehi et al., "Increased App Expression in a Mouse Model of Down's Syndrome Disrupts NGF Transport and Causes Cholinergic Neuron Degeneration," Neuron, 2006, 51:29-42.
Schliebs et al., "The significance of the cholinergic system in the brain during aging and in Alzheimer's disease," J. Neural. Transm., 2006, 113:1625-1644.
Shimada et al., "Mapping of brain acetylcholinesterase alterations in Lewy body disease by PET," Neurology, 2009, 73:273-278.
Spowart-Manning et al., "Spatial discrimination deficits by excitotoxic lesions in the Morris water escape task," Behavioural Brain Research, 2005, 156:269-276.
Steriade et al., "Neuronal activities in brain-stem cholinergic nuclei related to tonic activation processes in thalamocortical systems," Journal of Neuroscience, 1990, 10(8):2541-2559.
Submission Document in Chinese Patent Application No. 201880053052.1, dated Jul. 22, 2020, 14 pages (with English Translation).
Submission Document in Gulf Cooperation Council Patent Application No. GC2020-39301, dated Apr. 22, 2020, 9 pages (with English Translation).
Submission Document in Korean Patent Application No. 10-2020-7004232, dated May 22, 2020, 7 pages (with English Translation).
Submission Document in Vietnamese Patent Application No. 1-2020-00813, dated Jun. 22, 2020, 13 pages (with English Translation).
Tiraboschi, et al., "Cholinergic dysfunction in diseases with Lewy bodies," Neurology, 2000, 54:407-411.
Ustalar et al., "Microwave assisted synthesis of 2,3-dihydro-4H-benzo[4,5]thiazolo[3,2-a]furo[2,3-d]pyrimidin-4-ones and 6,7-dihydro-5H-furo[2,3-d]thiazolo[3,2-a]pyrimidin-5-ones using Mn(OAc)$_3$," Tetrahedron Letters, 2016, 58(6):516-519, ISSN 0040-4039.
Vana et al., "Progression of tan pathology in cholinergic Basal forebrain neurons in mild cognitive impairment and Alzheimer's disease," The American Journal of Pathology, 2011, 179(5):2533-2550.
Xu et al., "Amyloid precursor protein-mediated endocytic pathway disruption induces axonal dysfunction and neurodegeneration," The Journal of Clinical Investigation, 2016, 126(5):1815-1833.
Xu et al., "Memory deficits correlate with tau and spine pathology in P301S MAPT transgenic mice," Neuropathology and Applied Neurobiology, 2014, 40:833-843.
Yoshiyama et al., "Synapse loss and microglial activation precede tangles in a P301S tauopathy mouse model," Neuron, 2007, 53:337-351.
Submission Document in European Patent Application No. 18853415.0, dated Feb. 24, 2021, 6 pages.
Submission Document in Israeli Patent Application No. 272652, dated Mar. 11, 2021, 10 pages (with Partial Translation).
Submission Document in Vietnamese Patent Application No. 1-2020-00813, dated Feb. 23, 2021, 12 pages (with English Translation).
Notice of Allowance in Russian Patent Application No. 2020106798, dated Aug. 5, 2021, 20 pages (with English Translation).
Notice of Allowance in U.S. Appl. No. 16/807,335, dated Nov. 18, 2021, 4 pages.

(56) References Cited

OTHER PUBLICATIONS

Submission Document in U.S. Appl. No. 16/807,335, dated Nov. 9, 2021, 13 pages.
Office Action in Gulf Cooperation Council Patent Application No. GC2018-35952, dated Jul. 26, 2021, 53 pages (with English Translation).
Submission Document in Ukrainian Patent Application No. a202000934, dated Jul. 29, 2021, 10 pages (with English Translation).
Submission Document in Indian Patent Application No. 202047005838, dated Jul. 28, 2021, 7 pages.
Notice of Allowance in European Patent Application No. 18853415.0, dated Apr. 8, 2021, 50 pages.
Notice of Allowance in South African Patent Application No. 2020/00970, dated May 24, 2021, 2 pages.
Office Action in Argentine Patent Application No. 20200100583, dated Mar. 31, 2021, 18 pages (with English Translation).
Office Action in Chilean Patent Application No. 202000376, dated Mar. 15, 2021, 30 pages (with English Translation).
Office Action in Russian Patent Application No. 2020106798, dated Apr. 22, 2021, 15 pages (with English Translation).
Office Action in U.S. Appl. No. 16/807,335, dated May 18, 2021, 28 pages.
Submission Document in Chilean Patent Application No. 202000376, dated May 28, 2021, 85 pages (with English Translation).
Submission Document in Gulf Cooperation Council Patent Application No. GC2020-39301, dated Mar. 28, 2021, 12 pages (with English Translation).
Submission Document in Russian Patent Application No. 2020106798, dated Jun. 7, 2021, 14 pages (with English Translation).
Submission Document in Argentine Patent Application No. 20200100583, dated Jul. 23, 2021, 154 pages (with English Translation).
Submission Document in Indonesian Patent Application No. P00202001255, dated Jul. 30, 2021, 88 pages (with English Translation).
International Preliminary Report on Patentability in International Patent Application No. PCT/JP2020/008881, dated Sep. 16, 2021, 6 pages.
International Preliminary Report on Patentability in International Patent Application No. PCT/JP2020/008889, dated Sep. 16, 2021, 6 pages.
Office Action in U.S. Appl. No. 16/807,335, dated Sep. 16, 2021, 6 pages.
Notice of Allowance in Korean Patent Application No. 10-2020-7004232, dated Aug. 19, 2021, 4 pages (with English Translation).
Submission Document in U.S. Appl. No. 16/807,335, dated Aug. 17, 2021, 9 pages.
Notice of Allowance in U.S. Appl. No. 16/807,335, dated Oct. 27, 2021, 5 pages.
Submission Document in Gulf Cooperation Council Patent Application No. GC2018-35952, dated Oct. 17, 2021, 86 pages (with English Translation).
Notice of Allowance in U.S. Appl. No. 16/807,335, dated Aug. 30, 2021, 13 pages.
Office Action in Indian Patent Application No. 202047005838, dated Aug. 27, 2021, 6 pages (with English Translation).
Notice of Allowance in U.S. Appl. No. 16/807,335, dated Oct. 6, 2021, 4 pages.
Office Action in Gulf Cooperation Council Patent Application No. GC2020-39301, dated Oct. 24, 2021, 9 pages (with English Translation).
Submission Document in Brazilian Patent Application No. BR1120200031976, dated Jun. 29, 2021, 30 pages (with English Translation).
Official Notification in Chilean Patent Application No. 202000376, dated Jul. 21, 2021, 30 pages (with English Translation).
Submission Document in Australian Patent Application No. 2018330578, dated Sep. 10, 2021, 20 pages.
Notice of Allowance in Chilean Patent Application No. 202000376, dated Oct. 15, 2021, 10 pages (with English Translation).
Office Action in Chinese Patent Application No. 201880053052.1, dated Nov. 25, 2021, 10 pages (with English Translation).
Submission Document in Vietnamese Patent Application No. 1-2021-04971, dated Nov. 10, 2021, 14 pages (with English Translation).
Office Action in Vietnamese Patent Application No. 1-2021-04971 dated Sep. 24, 2021, 4 pages (with English Translation).
Office Action in Chinese Patent Application No. 202080014060.2, dated Aug. 31, 2021, 2 pages.
Office Action in Indonesian Patent Application No. P00202001255, dated Dec. 20, 2021, 9 pages (with English Translation).
Submission Document in Indonesian Patent Application No. P00202001255, dated Mar. 18, 2022, 9 pages (with English Translation).
Submission Document in Colombian Patent Application No. NC2020/0001471, dated Mar. 25, 2022, 20 pages (with English Translation).
Notice of Allowance in U.S. Appl. No. 16/807,335, dated Dec. 22, 2021, 5 pages.
Notice of Allowance in U.S. Appl. No. 16/807,335, dated Jan. 24, 2022, 4 pages.
Notice of Allowance in U.S. Appl. No. 16/807,335, dated Feb. 4, 2022, 4 pages.
Office Action in Colombian Patent Application No. NC2020/0001471, dated Jan. 7, 2022, 10 pages (with English Translation).
Office Action in Israeli Patent Application No. 272652, dated Feb. 1, 2022, 3 pages.
Office Action in Israeli Patent Application No. 285511, dated Mar. 2, 2022, 5 pages (with English Translation).
Official Notification in Colombian Patent Application No. NC2020/0001471, dated Dec. 29, 2021, 3 pages (with English Translation).
Submission Document in Chinese Patent Application No. 201880053052.1, dated Mar. 9, 2022, 20 pages (with English Translation).
Submission Document in Chinese Patent Application No. 202080014060.2, dated Feb. 14, 2022, 24 pages (with English Translation).
Submission Document in Indian Patent Application No. 202047005838, dated Feb. 23, 2022, 16 pages.
Submission Document in Singaporean Patent Application No. 11202001240X, dated Mar. 4, 2022, 11 pages.
Submission Document in Singaporean Patent Application No. 11202108780P, dated Feb. 21, 2022, 13 pages.
Submission Document in U.S. Appl. No. 16/807,335, dated Dec. 9, 2021, 14 pages.
Submission Document in U.S. Appl. No. 16/807,335, dated Jan. 26, 2022, 13 pages.
Notice of Allowance in Chinese Patent Application No. 201880053052.1, dated Mar. 28, 2022, 4 pages (with English Translation).
Notice of Allowance in U.S. Appl. No. 16/807,335, dated Mar. 16, 2022, 4 pages.
Submission Document in ARIPO (African Regional Intellectual Property Organization) Patent Application No. AP/P/2021/013417, dated Mar. 30, 2022, 5 pages.
Submission Document in Colombian Patent Application No. NC2021/0010512, dated Mar. 30, 2022, 10 pages (with English Translation).
Submission Document in European Patent Application No. 20766851.8, dated Mar. 24, 2022, 11 pages.
Submission Document in European Patent Application No. 20766918.5, dated Mar. 24, 2022, 11 pages.
Submission Document in Nigerian Patent Application No. NG/PT/PCT/2021/5674, dated Mar. 24, 2022, 5 pages.
Submission Document in South African Patent Application No. 2021/05729, dated Mar. 29, 2022, 11 pages.
Notice of Allowance in U.S. Appl. No. 16/807,335, dated Apr. 26, 2022, 4 pages.
Notice of Allowance in U.S. Appl. No. 16/807,335, dated Apr. 8, 2022, 6 pages.
Notice of Allowance in U.S. Appl. No. 16/807,335, dated May 12, 2022, 3 pages.
Submission Document in U.S. Appl. No. 16/807,335, dated Mar. 31, 2022, 14 pages.

* cited by examiner

SALT OF PENTACYCLIC COMPOUND AND CRYSTAL THEREOF

TECHNICAL FIELD

The present invention relates to pharmaceutically acceptable salts of a pentacyclic compound having cholinergic neuron activation and/or neuroprotective effect, as well as crystals of the pentacyclic compound and the pharmaceutically acceptable salts thereof. The present invention also relates to pharmaceutical compositions comprising the above salts or crystals as an active ingredient.

BACKGROUND ART

Cholinergic neurons which release acetylcholine as a transmitter are widely projected in the forebrain from the nucleus basalis of Meynert and the septal nucleus of the basal forebrain to the hippocampus, amygdala and cerebral cortex, and are involved in the modulation of memory; learning, cognition, and attention (Non-Patent Literature 1). Moreover, cholinergic neurons in the pedunculopontine tegmental nucleus and laterodorsal tegmental nucleus of the brain stem are projected in the striatum, accumbens nucleus, substantia nigra and thalamus, and are considered to be involved in the control of motivation and vigilance (Non-Patent Literatures 2 to 4).

In particular, the role of cholinergic neurons in the basal forebrain has been more clarified by analysis using many animal models such as lesion model. Especially, the correlation between functional disorder of cholinergic neurons and decreased memory and learning has been shown in the animal models (Non-Patent Literatures 5 to 7), and it has been shown that cognitive performance is improved by increasing the amount of acetylcholine using a cholinesterase inhibitor, and enhancing the function of cholinergic neurons (Non-Patent Literatures 8 to 12).

It has been reported that Nerve Growth Factor (NGF) shows the neuroprotective effect on cholinergic neurons in the animal model indicating loss of cholinergic neurons. (Non-Patent Literature 13 to 15).

Particularly for Alzheimer's disease (AD), loss of cholinergic neurons is found from early stage of AD and is one of the pathological features of AD. Accumulation of senile plaques by deposits of amyloid beta and neurofibrillary tangles by tau protein aggregation are also pathological features of AD, and particularly neurofibrillary tangles are known to increase with the progress of the disease status and bring neuronal death. Neurofibrillary tangles are found in nucleus basalis of Meynert and entorhinal cortex from the early stage of AD. Among them, it is reported that loss of cholinergic neurons in nucleus basalis of Meynert by tau protein aggregation is found at earlier stage and that there is a correlation between the loss and a decrease in cognitive function score (Non-Patent Literatures 16 and 17). Similarly to AD, hyperphosphorylation and abnormal accumulation of tau protein is found in genetically modified mice having a P301S mutation which has been found in familial frontotemporal dementia (human tau P301S transgenic mice). Consequently, neurofibrillary tangles, a pathological feature of AD, are thrilled (Non-Patent Literature 18) and bring cognitive dysfunction by synaptic impairment, neurodegeneration and loss of neurons. Based on these findings, human tau P301S transgenic mice are widely used as AD-like animal models (Non-Patent Literatures 19-22), and improvement of cognitive decline and suppression of disease status progress in Alzheimer's disease can be expected by suppressing AD-like pathological changes in human tau P301S transgenic mice.

Furthermore, multiple analyses using genetically modified mice and animal models of disorders suggest that axonal transport deficit is one of the causes of loss of cholinergic neurons (Non-Patent Literatures 23-25). Among them, the axon of cholinergic neurons which projects from septal area to hippocampus is impaired in a fimbria-fornix lesioned model and impairment of retrograde transport of molecules involved with survival and function brings loss of neurons (Non-Patent Literatures 26-28). The impairment of retrograde transport is found also in genetically modified mice (Non-Patent Literatures 23 and 24) and loss of cholinergic neurons by fimbria-fornix lesion reflects one aspect of the disease status. Accordingly; improvement of cognitive decline and suppression of disease status progress in Alzheimer's disease can be expected by suppression or improvement of loss of cholinergic neurons in this model of the disorder.

Dementia with Lewy bodies (DLB) and Parkinson disease (PD) are progressive neurodegenerative disorders in which abnormal inclusion bodies (Lewy bodies) mainly composed of alpha synuclein appear in neurons and bring degeneration and loss of neurons. Cognitive dysfunction develops if Lewy bodies are mainly distributed in cerebral cortex and Parkinsonism develops if Lewy bodies are mainly distributed in brain stem. In addition to that, psychiatric symptoms such as visual hallucination, hallucination and delusion, sleep disorder and autonomic symptoms also develop. The diagnosis is dementia with Lewy bodies if dementia appears before or within one year from the onset of Parkinsonism and the diagnosis is Parkinson disease with dementia (PDD) if Parkinsonism has appeared before one year or more from the onset of dementia. Dementia with Lewy bodies, Parkinson disease with dementia and Parkinson disease are pathologically same diseases and comprehensively referred to as Lewy body disease (LBD) though these are different in cognitive dysfunction and appearance order and degree of Parkinsonism. In dementia with Lewy bodies and Parkinson disease with dementia, similarly to Alzheimer's disease, neurons of nucleus basalis of Meynert, a nuclei of origin of cholinergic nerve, are degenerated and lost and it is reported that severe cholinergic neuron disorder appears in hippocampus and cortex (Non-Patent Literatures 29-31). Furthermore, there is a correlation between progress of cholinergic neuron disorder and cognitive dysfunction. (Non-Patent Literature 29), and cholinesterase inhibitors have been demonstrated to improve cognitive function. Based on these findings, cognitive function improves by the improvement of function of cholinergic neurons, and similarly to Alzheimer's disease, improvement of cognitive decline and suppression of disease status progress in dementia with Lewy bodies and Parkinson disease with dementia can be expected by suppression or improvement of loss of cholinergic neurons in several models of the disorder.

Therefore, based on these findings, an improvement in reduced cognitive performance caused by the dysfunction of cholinergic neurons can be expected by achieving functional activation and/or neuroprotective effect on cholinergic neurons in clinical practice.

CITATION LIST

Non Patent Literature

[Non-Patent Literature 1] Everitt B J et al. "Central cholinergic systems and cognition." Annu, Rev. Psychol. 48 (1997) 649-684.

[Non-Patent Literature 2] Gulledge A T, et al. "Cholinergic inhibition of neocortical pyramidal neurons." J. Neurosci. 25 (2005) 10308-20.

[Non-Patent Literature 3] Daniel Dautan D. et al. "A major external source of cholinergic innervation of the striatum and nucleus accumbens originates in the brainstem." J. Neurosci. 34 (2014) 4509-18.

[Non-Patent Literature 4] M Steriade M. et al. "Neuronal activities in brain-stem cholinergic nuclei related to tonic activation processes in thalamocortical systems." J. Neurosci, 10 (1990) 2541-59.

[Non-Patent Literature 5] Fischer W. et al. "Progressive decline in spatial learning and integrity of forebrain cholinergic neurons in rats during aging." Neurobiol Aging 13 (1992) 9-23.

[Non-Patent Literature 6] Leanza G et al. "Selective lesion of the basal forebrain cholinergic system by intraventricular 192 IgG-saporin: behavioural, biochemical and stereological studies in the rat." Eur. Neurosci, 7 (1995) 329-43.

[Non-Patent Literature 7] Leanza G. et al. "Selective immunolesioning of the basal forebrain cholinergic system disrupts short-terra memory in rats." Eur. J. Neurosci. 8 (1996) 1535-44.

[Non-Patent Literature 8] Ogura et al. "Donepezil, a centrally acting acetylcholinesterase inhibitor, alleviates learning deficits in hypocholinergic models in rats." Methods Find Exp Clin Pharmacol. 22 (2000) 89-95.

[Non-Patent Literature 9] Spowart-Manning L. et al. "Spatial discrimination deficits by excitotoxic lesions in the Morris water escape task." Behav Brain Res. 156 (2005) 269-76.

[Non-Patent Literature 10] Bruce A R et al. "Choline acetyltransferase activity and cognitive domain score of Alzheimer's patients." Neurobiol. Aging. 21(2000) 11-17

[Non-Patent Literature 11] Rogers S L. et al "The efficacy and safety of donepezil in patients with Alzheimer's disease: results of a US Multicentre, Randomized, Double-Blind, Placebo-Controlled Trial. The Donepezil Study Group." Dementia. 7 (1996) 293-303

[Non-Patent Literature 12] Mori E. et al. "Donepezil for dementia with Lewy bodies: a randomized, placebo-controlled trial." Ann Neurol. 72 (2012) 41-52

[Non-Patent Literature 13] Mufson E J. et al. "Human cholinergic basal forebrain: chemoanatomy and neurologic dysfunction." J. Chem. Neuroanat. 26 (2003) 233-242

[Non-Patent Literature 14] Mufson E J. et al. "Cholinergic system during the progression of Alzheimer's disease: therapeutic implication." Expert. Rev. Neurother. 8 (2008) 1703-1718

[Non-Patent Literature 15] Schliebs R. et al. "The significance of the Cholinergic system in the brain dining aging and in Alzheimer's disease." J. Neural. Transit 113 (2006) 1625-1644

[Non-Patent Literature 16] Vana L et "Progression of tau pathology in cholinergic Basal forebrain neurons in mild cognitive impairment and Alzheimer's disease." Am J Pathol. 179 (2011) 2533-2550.

[Non-Patent Literature 17] Gomez-Isla T et al. "Neuronal loss correlates with but exceeds neurofibrillary tangles in Alzheimer's disease." Ann Neurol. 41 (1997) 17-24.

[Non-Patent Literature 18] Lee V M et al, "Neurodegenerative tauopathies." Annu. Rev. Neurosci. 24 (2001) 1121-1159.

[Non-Patent Literature 19] Allen B et al. "Abundant tau filaments and nonapoptotic neurodegeneration in transgenic mice expressing human P301S tau protein." J. Neurosci. 22 (2002) 9340-9351.

[Non-Patent Literature 20] Xu et at "Memory deficits correlate with tau and spine pathology in P301S MAPT transgenic mice." Neuropathol. Neurobiol. 40 (2014) 833-43.

[Non-Patent Literature 21] Yoshiyama Y et al. "Synapse loss and microglial activation precede tangles in a P301S tauopathy mouse model." Neuron. 53 (2007) 337-351.

[Non-Patent Literature 22] Hofmann N A et al. "impaired plasticity of cortical dendritic spines in P301S tau transgenic mice." Acta Neuropathol Commun. 1 (2013) 82,

[Non-Patent Literature 23] Salehi. A et al. "Increased App Expression in a Mouse Model of Down's Syndrome Disrupts NGF Transport and Causes Cholinergic Neuron Degeneration" Neuron 51(2006) 29-42.

[Non-Patent Literature 24] Onishi T et al, "Early-onset cognitive deficits and axonal transport dysfunction in P301S mutant tau transgenic mice" Neuroscience Research 80 (2014) 76-85,

[Non-Patent Literature 25] Xu W et al. "Amyloid precursor protein-mediated endocytic pathway disruption induces axonal dysfunction and neurodegeneration" J. Clin. Invest. 126 (2016) 1815-33.

[Non-Patent Literature 26] Lapchak P A et al. "Effect of recombinant human nerve growth factor on presynaptic cholinergic function in rat hippocampal slices following partial septohippocampal lesions: measures of [$^3$H]acetylcholine synthesis, [$^3$H]acetylcholine release and choline acetyltransferase activity" Neuroscience 42 (1991) 639-49.

[Non-Patent Literature 27] Gilmor M L et al. "Coordinate expression of the vesicular acetylcholine transporter and choline acetyltransferase following septohippocampal pathway lesions" J. Neuromchem, 71 (1998) 2411-20.

[Non-Patent Literature 28] Gu H et al. "Recombinant human NGF-loaded microspheres promote survival of basal forebrain cholinergic neurons and improve memory impairments of spatial learning in the rat model of Alzheimer's disease with fimbria-fornix lesion" Neurosci. Lett, 453 (2009) 204-9.

[Non-Patent Literature 29] Shimada; H. et al., "Mapping of brain acetylcholinesterase alterations in Lewy body disease by PET" Neurology, vol. 73, pp. 273-278, 2009.

[Non-Patent Literature 30] Tiraboschi, P. et al., "Cholinergic dysfunction in diseases with Lewy bodies" Neurology 54 (2000) 407-411.

[Non-Patent Literature 31] Perry; E. K. et. "Neocortical cholinergic activities differentiate Lewy body dementia from classical Alzheimer's disease", NeuroReport, vol. 5, pp. 747-749 (1994).

SUMMARY OF INVENTION

Technical Problem

The present inventors have found that the compound represented by the following formula (5,10-dimethyl-5,6,9,10,11,12-hexahydropyrido[4",3":4',5']thieno[2',3':4,5]pyrimido[1,2-a]thieno[3,2-f][1,4]diazepine-4,13-dione, hereinafter, referred to as "the compound (I)") has cholinergic neuron activation and/or neuroprotective effect. Therefore, the compound (I) has a potential use as an agent for improving the reduced cognitive performance caused by the dysfunction of cholinergic neurons.

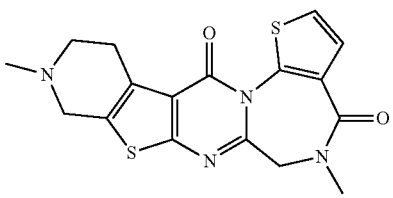

In general, physical properties of compounds used as pharmaceuticals and salts thereof, and crystals thereof greatly affect the bioavailability of the drug, the purity of the drug substance, and the formulation of the pharmaceutical preparation. Therefore, an object of the present invention is to provide pharmaceutically acceptable salts of the compound (I) having a potential use as a drug substance for pharmaceuticals, and crystals thereof:

Solution to Problem

As a result of diligent studies on the compound (I) in view of the above circumstances, the present inventors have found salts of the compound (I) and crystals thereof thereby completed the present invention.

That is, the present invention relates to the following <1> to <35>.

<1> A monohydrochloride or monohydrobromide of 5,10-dimethyl-5,6,9,10,11,12-hexahydropyrido[4",3":4',5']thieno[2',3':4,5]pyrimido[1,2-a]thieno[3,2-f][1,4]diazepine-4,13-dione represented by formula (I):

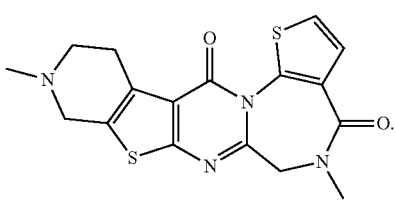

<2> A crystal of 5,10-dimethyl-5,6,9,10,11,12-hexahydropyrido[4",3":4',5']thieno[2',3':4,5]pyrimido[1,2-a]thieno[3,2-f][1,4]diazepine-4,13-dione or a monohydrochloride or monohydrobromide of 5,10-dimethyl-5,6,9,10,11,12-hexahydropyrido[4",3":4',5']thieno[2',3':4,5]pyrimido[1,2-a]thieno[3,2-f][1,4]diazepine-4,13-dione.

<3> A crystal of 5,10-dimethyl-5,6,9,10,11,12-hexahydropyrido[4",3":4',5']thieno[2',3':4,5]pyrimido[1,2-a]thieno[3,2-f][1,4]diazepine-4,13-dione having diffraction peaks at diffraction angles (2θ±0.2°) of 9.0°, 11.1° and 23.6° in a powder X-ray diffraction using CuKα as an X-ray source.

<3.1> A crystal of 5,10-dimethyl-5,6,9,10,11,12-hexahydropyrido[4",3":4',5']thieno[2',3':4,5]pyrimido[1,2-a]thieno[3,2-f][1,4]diazepine-4,13-dione having diffraction peaks at diffraction angles (2θ±0.2°) of 9.0°, 11.1°, 14.5°, 18.1°, 20.0°, 21.9°, 23.6°, 24.4°, 24.9° and 28.5° in a powder X-ray diffraction using CuKα as an X-ray source.

<3.2> A crystal of 5,10-dimethyl-5,6,9,10,11,12-hexahydropyrido[4",3": 4',5']thieno[2',3':4,5]pyrimido[1,2-a]thieno[3,2-f][1,4]diazepine-4,13-dione having the powder X-ray diffraction pattern of FIG. 1 in a powder X-ray diffraction using CuKα as an X-ray source.

<4> An A-type crystal of 5,10-dimethyl-5,6,9,10,11,12-hexahydropyrido[4",3":4',5']thieno[2',3':4,5]pyrimido[1,2-a]thieno[3,2-f][1,4]diazepine-4,13-dione monohydrochloride having diffraction peaks at diffraction angles (2θ±0.2°) of 11.6°, 20.8° and 25.7° in a powder X-ray diffraction using CuKα as an X-ray source.

<4,1> An A-type crystal of 5,10-dimethyl-5,6,9,10,11,12-hexahydropyrido[4",3":4',5']thieno[2',3':4,5]pyrimido[1,2-a]thieno[3,2-f][1,4]diazepine-4,13-dione monohydrochloride having diffraction peaks at diffraction angles (2θ±0.2°) of 6.1°, 7.8°, 11.6°, 16.2°, 19.9°, 20.8°, 25.2°, 25.7°, 26.9° and 29.9° in a powder X-ray diffraction using CuKα as an X-ray source.

<4.2> An A-type crystal of 5,10-dimethyl-5,6,9,10,11,12-hexahydropyrido[4",3":4',5']thieno[2',3':4,5]pyrimido[1,2-a]thieno[3,2-f][1,4]diazepine-4,13-dione monohydrochloride having the powder X-ray diffraction pattern of FIG. 2 in a powder X-ray diffraction using CuKα as an X-ray source.

<4.3> An A-type crystal of 5,10-dimethyl-5,6,9,10,11,12-hexahydropyrido[4",3":4',5']thieno[2',3':4,5]pyrimido[1,2-a]thieno[3,2-f][1,4]diazepine-4,13-dione monohydrochloride having peaks at chemical shifts (δ±0.5 ppm) of 164.0 ppm, 129.6 ppm and 36.5 ppm in a $^{13}C$ solid state NMR spectrum with glycine (176.03 ppm) as an external reference.

<5> A B-type crystal of 5,10-dimethyl-5,6,9,10,11,12-hexahydropyrido[4",3":4',5']thieno[2',3':4,5]pyrimido[1,2-a]thieno[3,2-f][1,4]diazepine-4,13-dione monohydrochloride having diffraction peaks at diffraction angles (2θ±0.2°) of 9.7°, 10.1° and 17.9° in a powder X-ray diffraction using CuKα as an X-ray source.

<5.1> A B-type crystal of 5,10-dimethyl-5,6,9,10,11,12-hexahydropyrido[4",3":4',5']thieno[2',3':4,5]pyrimido[1,2-a]thieno[3,2-f][1,4]diazepine-4,13-dione monohydrochloride having diffraction peaks at diffraction angles (2θ±0.2°) of 6.3°, 9.7°, 10.1°, 17.9°, 19.0°, 19.4°, 23.4°, 26.3°, 27.3° and 32.0° in a powder X-ray diffraction using CuKα as an X-ray source.

<5.2> A B-type crystal of 5,10-dimethyl-5,6,9,10,11,12-hexahydropyrido[4,3":4',5']thieno[2',3':4,5]pyrimido[1,2-a]thieno[3,2-f][1,4]diazepine-4,13-dione monohydrochloride having the powder X-ray diffraction pattern of FIG. 3 in a powder X-ray diffraction using CuKα as an X-ray source.

<5.3> A B-type crystal of 5,10-dimethyl-5,6,9,10,11,12-hexahydropyrido[4",3":4',5']thieno[2',3':4,5]pyrimido[1,2-a]thieno[3,2-f][1,4]diazepine-4,13-dione monohydrochloride having peaks at chemical shifts (δ±0.5 ppm) of 160.1 ppm, 133.4 ppm and 130.7 ppm in a $^{13}C$ solid state NMR spectrum with glycine (176.03 ppm) as an external reference.

<6> A C-type crystal of 5,10-dimethyl-5,6,9,10,11,12-hexahydropyrido[4",3":4',5']thieno[2',3':4,5]pyrimido[1,2-a]thieno[3,2-f][1,4]diazepine-4,13-dione monohydrochloride having diffraction peaks at diffraction angles (2θ±0.2°) of 6.0°, 7.7° and 16.9° in a powder X-ray diffraction using CuKα as an X-ray source.

<6.1> A C-type crystal of 5,10-dimethyl-5,6,9,10,11,12-hexahydropyrido[4",3":4',5']thieno[2',3':4,5]pyrimido[1,2-a]thieno[3,2-f][1,4]diazepine-4,13-dione monohydrochloride having diffraction peaks at diffraction angles (2θ±0.2°) of 6.0°, 7.7°, 9.7°, 11.4°, 15.8°, 16.9°, 18.1°, 23.2°, 25.4° and 27.6° in a powder X-ray diffraction using CuKα as an X-ray source.

<6.2> A C-type crystal of 5,10-dimethyl-5,6,9,10,11,12-hexahydropyrido[4",3":4',5']thieno[2',3':4,5]pyrimido[1,2-a]thieno[3,2-f][1,4]diazepine-4,13-dione monohydrochloride having the powder X-ray diffraction pattern of FIG. 4 in a powder X-ray diffraction using CuKα as an X-ray source.

<6.3> A C-type crystal of 5,10-dimethyl-5,6,9,10,11,12-hexahydropyrido[4",3":4',5']thieno[2',3':4,5]pyrimido[1,2-a]thieno[3,2-f][1,4]diazepine-4,13-dione monohydrochloride having peaks at chemical shifts (δ±0.5 ppm) of 159.6 ppm, 127.6 ppm and 38.9 ppm in a $^{13}C$ solid state NMR spectrum with glycine (176.03 ppm) as an external reference.

<7> A D-type crystal of 5,10-dimethyl-5,6,9,10,11,12-hexahydropyrido[4",3":4',5']thieno[2',3':4,5]pyrimido[1,2-a]thieno[3,2-f][1,4]diazepine-4,13-dione monohydrochloride having diffraction peaks at diffraction angles (2θ±0.2°) of 6.6°, 14.6° and 26.4° in a powder X-ray diffraction using CuKα as an X-ray source.

<7.1> A D-type crystal of 5,10-dimethyl-5,6,7,8,9,10,11,12-hexahydropyrido[4",3":4',5']thieno[2',3':4,5]pyrimido[1,2-a]thieno[3,2-f][1,4]diazepine-4,13-dione monohydrochloride having diffraction peaks at diffraction angles (2θ±0.2°) of 6.6°, 14.6°, 16.1°, 20.5°, 21.0°, 23.0°, 24.5°, 26.4°, 28.0° and 32.5° in a powder X-ray diffraction using CuKα as an X-ray source.

<7.2> A D-type crystal of 5,10-dimethyl-5,6,9,10,11,12-hexahydropyrido[4",3":4',5']thieno[2',3':4,5]pyrimido[1,2-a]thieno[3,2-f][1,4]diazepine-4,13-dione monohydrochloride having the powder X-ray diffraction pattern of FIG. 5 in a powder X-ray diffraction using CuKα as an X-ray source.

<8> An E-type crystal of 5,10-dimethyl-5,6,9,10,11,12-hexahydropyrido[4",3":4',5']thieno[2',3':4,5]pyrimido[1,2-a]thieno-[3,2-f][1,4]diazepine-4,13-dione monohydrochloride having diffraction peaks at diffraction angles (2θ±0.2°) of 6.4°, 11.3° and 27.3° in a powder X-ray diffraction using CuKα as an X-ray source.

<8.1> An E-type crystal of 5,10-dimethyl-5,6,9,10,11,12-hexahydropyrido[4",3":4',5']thieno[2',3':4,5]pyrimido[1,2-a]thieno[3,2-f][1,4]diazepine-4,13-dione monohydrochloride having diffraction peaks at diffraction angles (2θ±0.2°) of 6.4°, 11.3°, 15.7°, 18.0°, 19.2°, 22.8°, 24.6°, 25.4°, 26.0° and 27.3° in a powder X-ray diffraction using CuKα as an X-ray source.

<8.2> An E-type crystal of the compound (I) monohydrochloride having the powder X-ray diffraction pattern of FIG. 6 in a powder X-ray diffraction using CuKα as an X-ray source.

<9> An F-type crystal of 5,10-dimethyl-5,6,9,10,11,12-hexahydropyrido[4",3":4',5']thieno[2',3':4,5]pyrimido[1,2-a]thieno[3,2-f][1,4]diazepine-4,13-dione monohydrochloride having diffraction peaks at diffraction angles (2θ±0.2°) of 7.3°, 9.3° and 10.7° in a powder X-ray diffraction using CuKα as an X-ray source.

<9.1> An F-type crystal of 5,10-dimethyl-5,6,9,10,11,12-hexahydropyrido[4",3":4',5']thieno[2',3':4,5]pyrimido[1,2-a]thieno[3,2-f][1,4]diazepine-4,13-dione monohydrochloride having diffraction peaks at diffraction angles (2θ±0.2°) of 5.9°, 7.3°, 9.3°, 10.7°, 13.8°, 15.6°, 16.4°, 18.7°, 25.1° and 26.8° in a powder X-ray diffraction using CuKα as an X-ray source.

<9.2> An F-type crystal of 5,10-dimethyl-5,6,9,10,11,12-hexahydropyrido[4",3":4',5']thieno[2',3':4,5]pyrimido[1,2-a]thieno[3,2-f][1,4]diazepine-4,13-dione monohydrochloride having the powder X-ray diffraction pattern of FIG. 7 in a powder X-ray diffraction using CuKα as an X-ray source.

<10> A crystal of 5,10-dimethyl-5,6,9,10,11,12-hexahydropyrido[4",3":4',5']thieno[2',3':4,5]pyrimido[1,2-a]thieno[3,2-f][1,4]diazepine-4,13-dione monohydrobromide having diffraction peaks at diffraction angles (2θ±0.2°) of 7.8°, 24.5° and 25.2° in a powder X-ray diffraction using CuKα as an X-ray source.

<10.1> A crystal of 5,10-dimethyl-5,6,9,10,11,12-hexahydropyrido[4",3":4',5']thieno[2',3';4,5]pyrimido[1,2-a]thieno[3,2-f][1,4]diazepine-4,13-dione monohydrobromide having diffraction peaks at diffraction angles (2θ±0.2°) of 6.0°, 7.8°, 10.0°, 11.7°, 17.8°, 20.8°, 23.5°, 24.5°, 25.2° and 27.3° in a powder X-ray diffraction using CuKα as an X-ray source.

<10.2> A crystal of 5,10-dimethyl-5,6,9,10,11,12-hexahydropyrido[4",3":4',5']thieno[2',3':4,5]pyrimido[1,2-a]thieno[3,2-f][1,4]diazepine-4,13-dione monohydrobromide having the powder X-ray diffraction pattern of FIG. 8 in a powder X-ray diffaction using CuKα as an X-ray source.

<11> An A-type crystal of 5,10-dimethyl-5,6,9,10,11,12-hexahydropyrido[4",3":4',5']thieno[2',3':4,5]pyrimido[1,2-a]thieno[3,2-f][1,4]diazepine-4,13-dione monohydrochloride having a Raman shift peak (±2 $cm^{-1}$) at 587 $cm^{-1}$ in a Raman spectroscopy measurement.

<12> An A-type crystal of 5,10-dimethyl-5,6,9,10,11,12-hexahydropyrido[4",3":4',5']thieno[2',3':4,5]pyrimido[1,2-a]thieno[3,2-f][1,4]diazepine-4,13-dione monohydrochloride having Raman shift peaks (±2 $cm^{-1}$) at 587 $cm^{-1}$, 1428 $cm^{-1}$ and 1493 $cm^{-1}$ in a Raman spectroscopy measurement.

<13> An A-type crystal of 5,10-dimethyl-5,6,9,10,11,12-hexahydropyrido[4",3":4',5']thieno[2',3':4,5]pyrimido[1,2-a]thieno[3,2-f][1,4]diazepine-4,13-dione monohydrochloride having Raman shill peaks (±2 $cm^{-1}$) at 587 $cm^{-1}$, 763 $cm^{-1}$, 1428 $cm^{-1}$, 1493 aril and 1688 $cm^{-1}$ in a Raman spectroscopy measurement.

<14> An A-type crystal of 5,10-dimethyl-5,6,9,10,11,12-hexahydropyrido[4",3":4',5']thieno[2',3':4,5]pyrimido[1,2-a]thieno[3,2-f][1,4]diazepine-4,13-dione monohydrochloride having Raman shift peaks (±2 $cm^{-1}$) at 409 $cm^{-1}$, 587 $cm^{-1}$, 763 $cm^{-1}$, 976 $cm^{-1}$, 1.478 $cm^{-1}$, 1491 $cm^{-1}$ and 1688 $cm^{-1}$ in a Raman spectroscopy measurement.

<15> An A-type crystal of 5,10-dimethyl-5,6,9,10,11,12-hexahydropyrido[4",3":4',5']thieno[2',3':4,5]pyrimido[1,2-a]thieno[3,2-f][1,4]diazepine-4,13-dione monohydrochloride having the spectrum of FIG. 19 in a Raman spectroscopy measurement.

<16> A pharmaceutical composition comprising the salt according to <1> or the crystal according to any one of <2> to <15>.

<17> The pharmaceutical composition according to <16>, which is a cholinergic neuron activating agent.

<18> The pharmaceutical composition according to <16>, which is a cholinergic neuron protecting agent.

<19> The pharmaceutical composition according to <16> for the treatment of cognitive dysfunction.

<20> A therapeutic agent for cognitive dysfunction comprising the salt according to <1> or the crystal according to any one of <2> to <15>.

<21> A method of treating cognitive dysfunction, comprising administering the salt according to <1> or the crystal according to any one of <2> to <15> to a patient.

<22> The salt according to <1> or the crystal according to any one of <2> to <15> for use in the treatment of cognitive dysfunction.

<23> Use of the salt according to <1> or the crystal according to any one of <2> to <15> for the manufacture of a therapeutic agent for cognitive dysfunction.

<24> A therapeutic agent for Alzheimer's disease comprising the salt according to <1> or the crystal according to any one of <2> to <15>.

<25> A method of treating Alzheimer's disease, comprising administering the salt according to <1> or the crystal according to any one of <2> to <15> to a patient.

<26> The salt according to <1> or the crystal according to any one of <2> to <15> for use in the treatment of Alzheimer's disease.
<27> Use of the salt according to <1> or the crystal according to any one of <2> to <15> for the manufacture of a therapeutic agent for Alzheimer's disease.
<28> A therapeutic agent for Dementia with Lewy bodies comprising the salt according to <1> or the crystal according to any one of <2> to <15>.
<29> A method of treating Dementia with Lewy bodies, comprising administering the salt according to <1> or the crystal according to any one of <2> to <15> to a patient.
<30> The salt according to <1> or the crystal according to any one of <2> to <15> for use in the treatment of Dementia with Lewy bodies.
<31> Use of the salt according to <1> or the crystal according to any one of <2> to <15> for the manufacture of a therapeutic agent for Dementia with Lewy bodies.
<32> A therapeutic agent for Parkinson disease with dementia comprising the salt according to <1> or the crystal according to any one of <2> to <15>.
<33> A method of treating Parkinson disease with dementia, comprising administering the salt according to <1> or the crystal according to any one of <2> to <15> to a patient.
<34> The salt according to <1> or the crystal according to any one of <2> to <15> for use in the treatment of Parkinson disease with dementia.
<35> Use of the salt according to <1> or the crystal according to any one of <2> to <15> for the manufacture of a therapeutic agent for Parkinson disease with dementia.

Advantageous Effects of Invention

According to the present invention, salts of the compound (I) and crystals thereof that are expected to have a potential use as drug substances of pharmaceuticals and have good physical properties can be provided.

DESCRIPTION OF EMBODIMENTS

Figure 1:
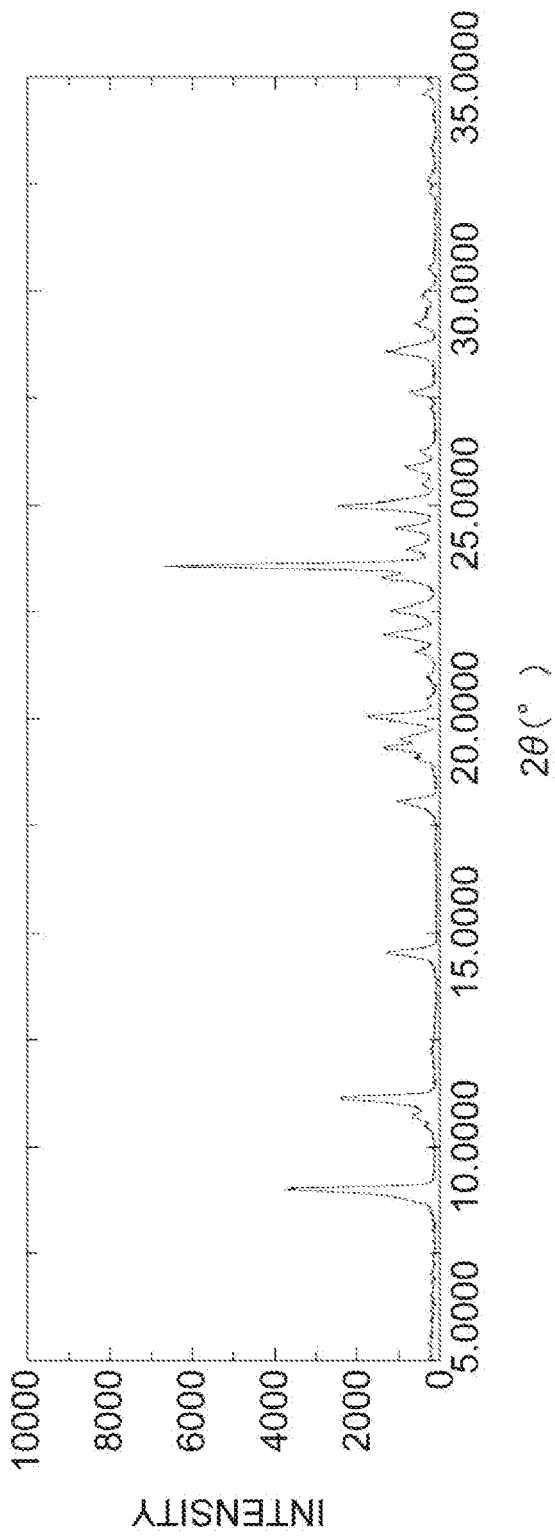
FIG. 1 is a powder X-ray diffraction pattern of the crystal of the compound (I) Obtained in Example 1. The abscissa represents the diffraction angle (2θ) and the ordinate represents the peak intensity.

Hereinafter, salts of the compound (I) of the present invention, crystals thereof and a production method thereof will be described in detail.
As used herein, the "salt" refer to a chemical substance consisting of the compound (I) as a basic component and a certain number of equivalents of acid relative to the compound (I).

Examples of the "salt" as used herein include salts with inorganic acids, salts with organic acids, and salts with acidic amino acids, and among these, pharmaceutically acceptable salts are preferable.

Examples of the salts with inorganic acids include salts with hydrochloric acid, hydrobromic acid, sulfuric acid, nitric acid and phosphoric acid; and examples of the salts with organic acids include salts with organic carboxylic acids such as acetic acid, succinic acid, fumaric acid, maleic acid, tartaric acid, malic acid, citric acid, lactic acid, stearic acid and benzoic acid, and salts with organic sulfonic acids such as methanesulfonic acid (mesylate), ethanesulfonic acid, benzenesulfonic acid and p-toluenesulfonic acid (tosylate); and among these, hydrochloric acid, hydrobromic acid and phosphoric acid are preferable.

Examples of the salts with acidic amino acids include salts with aspartic acid and glutamic acid.

The salt of the present invention may be an anhydrate, or a hydrate or a solvate. The hydrate or the solvate as used herein refer to a solid that the compound (I) or the salt thereof and water molecules or solvent molecules together form; and the solid may be a crystal; and examples of the solvent of the solvate include ketone-based solvents such as acetone, 2-butanone and cyclohexanone; ester-based solvents such as methyl acetate and ethyl acetate; ether-based solvents such as 1,2-dimethoxyethane and t-butylmethylether; alcohol-based solvents such as methanol, ethanol, 1-propanol and isopropanol; polar solvents such as N-methyl-2-pyrrolidone, N,N-dimethylfomamide and dimethylsulfoxide. The number of water molecules or solvent molecules to the compound (I) or the salt thereof is not particularly limited, and for example, it may be one molecule or two molecules.

As used herein, the "crystal" refer to the crystal of an anhydrate or a hydrate of the compound (I) or the salt thereof.

Figure 19:
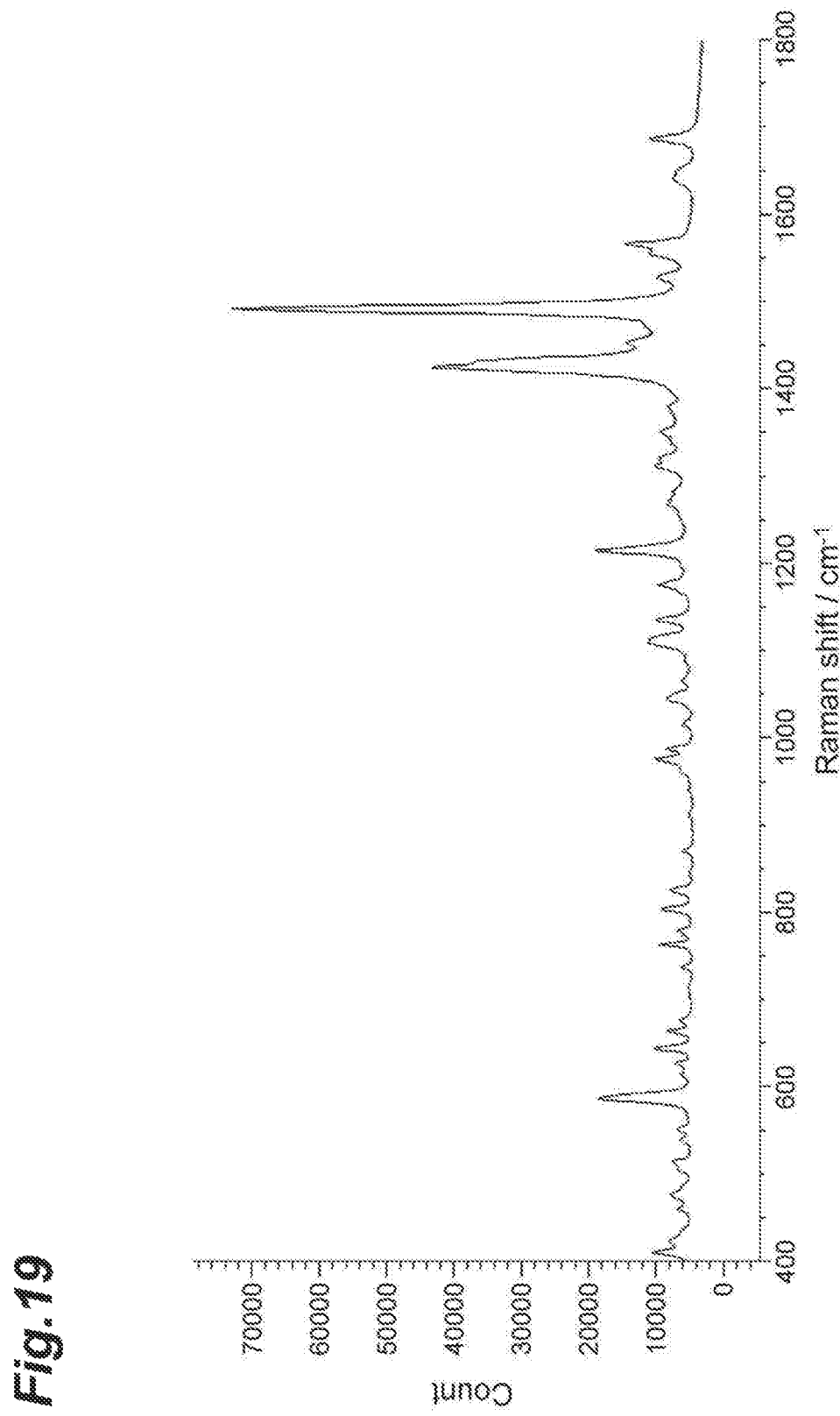
FIG. 19 shows a Raman spectrum of the A-type crystal of the compound (I) monohydrochloride Obtained in Example 2.

As used herein, preferable examples of the crystal of the compound (I) and the hydrochloride and the hydrobromide of the compound (I) include:

a crystal of the compound (I) having diffraction peaks at diffraction angles (2θ±0.2°) of 9.0°, 11.1° and 23.6° in a powder X-ray diffraction;

a crystal of the compound (I) having diffraction peaks at diffraction angles (2θ±0.2°) of 9.0°, 11.1°, 14.5°, 18.1°, 20.0°, 21.9°, 23.6°, 24.4°, 24.9 and 28.5° in a powder X-ray diffraction;

an A-type crystal of the compound (I) monohydrochloride having diffraction peaks at diffraction angles (2θ±0.2°) of 11.6°, 20.8° and 25.7° in a powder X-ray diffraction;

an A-type crystal of the compound (I) monohydrochloride having diffraction peaks at diffraction angles (2θ±0.2°) of 6.1°, 7.8°, 11.6°, 16.2°, 19.9°, 20.8°, 25.2°, 25.7°, 26.9° and 29.9° in a powder X-ray diffraction;

an A-type crystal of the compound (I) monohydrochloride having peaks at chemical shifts (δ±0.5 ppm) of 164.0 ppm, 129.6 ppm and 36.5 ppm in a $^{13}$C solid state NMR spectrum;

an A-type crystal of the compound (I) monohydrochloride having a Raman shift peak (±2 cm$^{-1}$) at 587 cm$^{-1}$ in a Raman spectroscopy measurement;

an A-type crystal of the compound (I) monohydrochloride having Raman shift peaks (±2 cm$^{-1}$) at 587 cm$^{-1}$, 1428 cm$^{-1}$ and 1493 cm$^{-1}$ in a Raman spectroscopy measurement;

an A-type crystal of the compound (I) monohydrochloride having Raman shift peaks (±2 cm$^{-1}$) at 587 cm$^{-1}$, 763 cm$^{-1}$, 1428 cm$^{-1}$, 1493 cm$^{-1}$ and 1688 cm$^{-1}$ in a Raman spectroscopy measurement;

an A-type crystal of the compound (I) monohydrochloride having Raman shift peaks (±2 cm$^{-1}$) at 409 cm$^{-1}$, 587 cm$^{-1}$, 763 cm$^{-1}$, 976 cm$^{-1}$, 1428 cm$^{-1}$, 1493 cm$^{-1}$ and 1688 cm$^{-1}$ in a Raman spectroscopy measurement;

an A-type crystal of the compound (I) monohydrochloride substantially having a spectrum shown in FIG. 19 in a Raman spectroscopy measurement;

a B-type crystal of the compound (I) monohydrochloride having diffraction peaks at diffraction angles (2θ±0.2°) of 9.7°, 10.1° and 17.9° in a powder X-ray diffraction;

a B-type crystal of the compound (I) monohydrochloride having diffraction peaks at diffraction angles (2θ±0.2°) of 6.3°, 9.7°, 10.1°, 179°; 19.0°, 19.4°, 23.4°, 26.3°, 27.3° and 32.0° in a powder X-ray diffraction;

a B-type crystal of the compound (I) monohydrochloride having peaks at chemical shifts (δ±0.5 ppm) of 160.1 ppm, 133.4 ppm and 130.7 ppm in a $^{13}$C solid state NMR spectrum;

a C-type crystal of the compound (I) monohydrochloride having diffraction peaks at diffraction angles (2θ±0.2°) of 6.0°, 7.7° and 16.9° in a powder X-ray diffraction;

a C-type crystal of the compound (I) monohydrochloride having diffraction peaks at diffraction angles (2θ±0.2°) of 6.0°, 7.7°, 9.7°, 11.4°, 15.8°, 16.9°, 18.1°, 23.2°, 25.4° and 27.6° in a powder X-ray diffraction;

a C-type crystal of the compound (I) monohydrochloride having peaks at chemical shifts (δ±0.5 ppm) of 159.6 ppm, 127.6 ppm and 38.9 ppm in a $^{13}$C solid state NMR spectrum;

a D-type crystal of the compound (I) monohydrochloride having diffraction peaks at diffraction angles (2θ±0.2°) of 6.6°, 14.6° and 26.4° in a powder X-ray diffraction;

a D-type crystal of the compound (I) monohydrochloride having diffraction peaks at diffraction angles (2θ±0.2°) of 6.6°, 14.6°, 16.1°, 20.5°, 21.0°, 23.0°, 24.5°, 26.4°, 28.0° and 32.5° in a powder X-ray diffraction;

an E-type crystal of the compound (I) monohydrochloride having diffraction peaks at diffraction angles (2θ±0.2°) of 6.4°, 11.3° and 27.3° in a powder X-ray diffraction;

an E-type crystal of the compound (I) monohydrochlorde having diffraction peaks at diffraction angles (2θ±0.2°) of 6.4°, 11.3°, 15.7°, 18.0°, 19.2°, 22.8°, 24.6°, 25.4°, 26.0° and 27.3° in a powder X-ray diffraction;

an F-type crystal of the compound (I) monohydrochloride having diffraction peaks at diffraction angles (2θ±0.2°) of 7.3°, 9.3° and 10.7° in a powder X-ray diffraction;

an F-type crystal of the compound (I) monohydrochloride having diffraction peaks at diffraction angles (2θ±0.2°) of 5.9°, 7.3°, 9.3°, 10.7°, 13.8°, 15.6°, 16.4°, 18.7°, 25.1° and 26.8° in a powder X-ray diffraction;

a crystal of the compound (I) monohydrobromide having diffraction peaks at diffraction angles (2θ±0.2°) of 7.8°, 24.5° and 25.2° in a powder X-ray diffraction; and a crystal of the compound (I) monohydrobromide having diffraction peaks at diffraction angles (2θ±0.2°) of 6.0°, 7.8°, 10.0°, 11.7°, 17.8°, 20.8°, 23.5°, 24.5°, 25.2° and 27.3° in a powder X-ray diffraction.

The diffraction peaks in the powder X-ray diffraction, the chemical shifts in the $^{13}$C solid state NMR spectrum, and the Raman shift peaks in the Raman spectroscopy measurement, described above, are unique to each of the crystal of the compound (I), the A to F-type crystals of the compound (I) monohydrochloride, and the crystal of the compound (I) monohydrobromide, and they are characteristic peaks for the crystals.

In general, the diffraction angles (2θ) in the powder X-ray diffraction may contain errors within the range of ±0.2°, so that the values of the diffraction angles described above need to be considered to include numerical values within the range of about ±0.2°. Thus, not only crystals whose diffraction angles of the peaks in the powder X-ray diffraction perfectly match, but also crystals whose diffraction angles of the peaks match within an error of about ±0.2° are the same in a certain compound or the salt thereof and included in the present invention.

As used herein, for example, "having a diffraction peak at a diffraction angle (2θ±0.2°) of 9.0°" means "having a diffraction peak at a diffraction angle (2θ) of 8.8° to 9.2°", and the same applies to the case of other diffraction angles.

In general, even when the crystalline form is the same, the peak intensity or the half-width of the diffraction angles (2θ) in the powder X-ray diffraction is different for each measurement depending on different measurement conditions and variations in size and form of the particles of the powder crystals used as a measurement sample, and a constant peak intensity or half-width is not always shown. Hence, in comparing the powder X-ray diffraction patterns, when there is a difference in peak intensity or half-width at the same diffraction angle (2θ), it does not mean that the difference derives from the difference of crystalline forms. Thus, it means that the crystal having a powder X-ray diffraction pattern which has such differences with respect to the diffraction peak characteristic of the specific crystal of the present invention has the same crystalline form as the crystal of the present invention. In addition, as used herein, "having the powder X-ray diffraction pattern of FIG. 1" means that all the crystal showing the powder X-ray diffraction pattern shown in FIG. 1 is the same crystal as the crystal of the present invention, not only in the case where a powder X-ray diffraction pattern having characteristic diffraction peaks matches the powder X-ray diffraction pattern shown in FIG. 1 within the error range of ±0.2°, but also in the case of a powder X-ray diffraction pattern having different peak intensity or half-width while having characteristic diffraction angles that match the powder X-ray diffraction pattern shown in FIG. 1 within the error range of ±0.2°.

As used herein, "chemical shifts (δ±0.5 ppm) of 16.4.0 ppm, 129.6 ppm and 36.5 ppm" mean "to have peaks substantially equivalent to chemical shifts (δ±0.5 ppm) of 164.0 ppm, 129.6 ppm and 36.5 ppm when a $^{13}$C solid state NMR spectrum measurement is carried out under the usual measurement conditions or under the conditions substantially the same as the present specification".

In general, in determining whether or not "to have peaks substantially equivalent to", the chemical shift δ in the $^{13}$C, solid state NMR spectrum may contain errors within the range of ±0.5 ppm, so that the values of the chemical shifts described above need to be considered to include numerical values within the range of about ±0.5 ppm. Thus, not only crystals whose chemical shifts in the $^{13}$C solid state NMR spectrum perfectly match, but also crystals whose chemical shifts match within an error of about ±0.5 ppm are included in the present invention. Hence, as used herein, for example, "having a peak at a chemical shift (δ±0.5 ppm) of 164.0 ppm" means having a peak at a Chemical shift (δ) within the range of 163.5 ppm to 164.5 ppm and the same applies to the case of other chemical shifts in the $^{13}$C solid state NAIR spectrum.

In general, the Raman shift peaks ($cm^{-1}$) in the Raman spectroscopy measurement may contain errors within the range of ±2 $cm^{-1}$, so that the values of die peaks described above need to be considered to include numerical values within the range of about ±2 $cm^{-1}$. Thus, not only crystals whose Raman shift peaks in the Raman spectroscopy measurement perfectly match, but also crystals whose Raman shift peaks match within an error of about ±2 $cm^{-1}$ are the same in a certain compound or the salt thereof and included in the present invention.

As used herein, for example, "having a Raman shift peak (±2 $cm^{-1}$) at 587 $cm^{-1}$ in a Raman spectroscopy measurement" means "having a Raman shill peak at 585 $cm^{-1}$ to 589 $cm^{-1}$ in a Raman spectroscopy measurement", and the same applies to the case of other Raman shifts.

In general, even when the crystalline form is the same, the peak intensity or the half-width of the Raman shill in the Raman spectroscopy measurement is different for each measurement depending on different measurement conditions and variations in size and form of the particles of the powder crystals used as a measurement sample, and a constant peak intensity or half-width is not always shown. Hence, in comparing the Raman spectroscopy measurements, when there is a difference in peak intensity or half-width at the same Raman shift peak ($cm^{-1}$), it does not mean that the difference derives from the difference of crystalline forms. Thus, it means that the crystal having a Raman spectrum which has such differences with respect to the Raman shift peaks characteristic of a certain crystal of the present invention has the same crystalline form as the crystal of the present invention. In addition, as used herein, "having the spectrum of FIG. 19 in a Raman spectroscopy measurement" means that all the crystal showing the Raman spectrum shown in FIG. 19 is the same crystal as the crystal of the present invention, not only in the case where a Raman spectrum having characteristic Raman shill peaks ($cm^{-1}$) matches the Raman spectrum shown in FIG. 19 within the error range of ±2 $cm^{-1}$, but also in the case of a Raman spectrum having different peak intensities or half-widths despite of having characteristic Raman shift peaks that match within the error range of ±2 $cm^{-1}$.

Hereinafter, methods for producing salts of the compound (I), crystals, and the like, which are one embodiment of the present invention, will be described.

Method for Producing Compound (I)

The compound (I) may be one produced by methods well-known to those skilled in the art. For example, the compound (I) can be synthesized by a method described in Reference Example described later Method for Producing Salt of Compound (I)

The salts of the compound (I) according to the present invention can be obtained by methods for producing ordinary salts. Specifically, the salts can be produced by, for example, suspending or dissolving the compound (I) into a solvent, while heating as necessary, and then adding an acid into the resulting suspension or solution, followed by stirring or allowing the mixture to stand at room temperature or while cooling for several minutes to several days. By using these production methods, the salts of the compound (I) can be obtained as crystalline or amorphous forms. Moreover, the amorphous form can be obtained by performing an operation such as lyophilization in addition to these production methods as necessary. Examples of the solvent used herein include alcohol-based solvents such as ethanol, 1-propanol and isopropanol; acetonitrile; ketone-based solvents such as acetone and 2-butanone; ester-based solvents such as ethyl acetate; saturated hydrocarbon-based solvents such as hexane and heptane; ether-based solvents such as t-butylmethylether and water. These solvents may be used singly or in combination of two or more thereof.

Method for Producing Crystal of Compound (I) or Salt Thereof

The crystal of the compound (I) or the salt thereof can be produced by the aforementioned method for producing the compound (I), or the method fir producing the salt thereof or can be produced by heating and dissolving the compound (I) or the salt thereof in a solvent and then cooling the resulting solution while stirring for crystallization.

The compound (I) or the salt thereof used for crystallization may be any form, that is, may be a solvate or a hydrate or an anhydrate, amorphous or crystalline forms (including one consisting of a plurality of polymorphic crystal), or the mixture thereof.

Examples of the solvent used for crystallization include alcohol-based solvents such as methanol; ethanol, isopropanol and 1-propanol; acetonitrile; amide-based solvents such as N,N-dimethylformamide; ester-based solvents such as ethyl acetate; saturated hydrocarbon-based solvents such as hexane and heptane; ketone-based solvents such as acetone and 2-butanone; ether-based solvents such as t-butylmethylether and water. These solvents may be used singly or in combination of two or more thereof.

The amount of the solvent to be used can be appropriately selected, provided that an amount capable of dissolving the compound (I) or the salt thereof by heating or an amount that enables the suspension to be stirred is the lower limit and an amount with which the yield of the crystal is not significantly reduced is the upper limit.

In the crystallization, a seed crystal (for example, the desired crystal of the compound (I) or the salt thereof) may be added or not be added. The temperature at which the seed crystal is added is not particularly limited, and preferably 0 to 80° C.

The temperature for heating and dissolving the compound (I) or the salt thereof may be appropriately selected depending on a solvent such that the compound (I) or the salt thereof can be dissolved at the temperature, but the temperature is preferably within the range of 50° C. to the temperature at which a recrystallization solvent starts to reflux; more preferably 55 to 80° C.

Since rapid cooling may produce crystals in different aspects (polymorphism), the cooling during crystallization is desirable to be carried out by appropriately controlling the cooling rate in consideration of the effect on quality and grade of the crystals, and is preferably cooling at a rate of for example, 5 to 40° C./hour. More preferably; it is cooling at a rate of, for example, 5 to 25° C./hour.

The final crystallization temperature may be appropriately selected depending on the yield, the quality, and the like of the crystals, and is preferably −25 to 30° C.

The target crystal can be obtained by separating the crystal obtained by crystallization by an ordinary filtration procedure, washing the filtered crystal with a solvent if necessary; and then drying. As the solvent to be used for washing the crystal, those similar to the solvents used for crystallization can be used. Preferably; examples thereof include ethanol, acetone, 2-butanone, ethyl acetate, diethylether, t-butylmethylether and hexane. These solvents may be used singly or in combination of two or more thereof.

The crystal separated by the filtration procedure can be dried by appropriately leaving in the air or under a nitrogen stream, or by heating.

The drying time may be appropriately selected as the time until the amount of the residual solvent falls below a predetermined amount, depending on the production amount, the drying apparatus, the drying temperature, and the like. Drying may also be carried out under airflow or under reduced pressure. The degree of pressure reduction may be appropriately selected depending on the production amount, the drying apparatus, the drying temperature, and the like. The resulting crystal may also be left in the air as necessary after drying.

The crystal of the compound (I) and salts of the compound (I) obtained by the production method described above have cholinergic neuron activation and/or neuroprotective effect, as shown in activity data in pharmacological test examples described later, and have a potential use as an agent for improving the reduced cognitive performance caused by the dysfunction of cholinergic neurons.

[Pharmaceutical Composition]

Another embodiment of the present invention is a pharmaceutical composition comprising the crystal of the compound (I) and pharmaceutically acceptable additives. A pharmaceutical composition can be produced by admixing pharmaceutically acceptable additives with the crystal of the compound (I). The pharmaceutical composition according to the present invention can be produced in accordance with a known method, for example, the method described in General Rules for Preparations in the Japanese Pharmacopoeia 17th Edition.

The pharmaceutical composition according to the present embodiment can be appropriately administered to a patient depending on the dosage firm thereof.

The dose of the compounds (I) according to the present invention varies depending on the severity of symptoms, age, sex, body weight, dosage form, type of salt, specific type of disease, and other conditions; however, in general, the dose for an adult per day by oral administration is about 30 to 10 g, preferably 100 μg to 5 g, and more preferably 100 μg to 1 g; the dose for an adult per day by injection administration is about 30 μg to 1 g, preferably 100 μg to 500 mg, and more preferably 100 μg to 300 mg; and the above dose is administered once or several firms.

EXAMPLES

The crystal of the compound (T) of the present invention can be produced by, for example, the methods described in the following Examples, and the effect of the compound can be confirmed by the methods described in the following Test Examples. However, these are just examples, and the present invention is not limited to the following specific examples in any case and may be modified within a range that does not depart from the scope of the present invention.

The powder X-ray crystal diffraction of the crystals produced in the following Examples was carried out by mounting the obtained crystal onto the sample stage of a powder X-ray diffraction apparatus and measured under any of the following conditions.

(Transmission Conditions)
X-ray source: CuKα
Voltage: 45 kV
Current: 40 mA
Optical system: focusing mirror
Soller slit: 0.02°
Detector: X'Celerator (semiconductor detector)
Scan range: 5° to 35°
Step size: 0.017°
Scan step time: 600 sec
Sample holder: kapton film
(Reflection Conditions)
X-ray source: CuKα
Voltage: 50 kV
Current: 300 mA
Slit: divergence slit 0.5 mm, scattering slit open, light receiving slit open Detector: scintillation counter
Scan rate: 5°/min
Sampling interval: 0.02°
Scan range: 5° to 35°
Sample holder: aluminum holder A sample was precisely weighed in an aluminum sample pan and the thermal analysis was carried out under the following conditions,
(Measurement Conditions)
Atmosphere: under nitrogen gas stream (100 mL/min)
Control: empty aluminum sample pan
Temperature rising rate: 10° C./min
Sampling interval: 1 sec
Measurement temperature range: room temperature to 320° C.

The $^{13}$C solid state NMR spectrum of the crystal was measured by enclosing about 300 mg of a solid sample into a sample tube under the following conditions.
(Measurement Conditions)
Apparatus used: Avance 400 MHz (manufactured by BRUKER) 7 mm-CPMAS probe (manufactured by BRUKER)
Nuclei measured: $^{13}$C (resonance frequency 100.6248425 MHz)
Measurement temperature: room temperature
Pulse mode: CPTOSS measurement
Rotational speed: 5000 Hz
Pulse repeating time: 3 sec
Contact time: 1 msec
Cumulative number of times: 5120 times
Reference material: glycine (external reference: 176.03 ppm)

The Raman spectrum of the crystals was measured by placing a sample onto the sample stage of a Raman microspectroscope under the following measurement conditions.
(Measurement Conditions)
Apparatus used: RENISHAW Raman Microscope in Via Reflex
Laser wavelength: 785 nm
Diffraction grating: 1200 lines/mm
Objective: 50 times
Scan mode: continuous
Exposure time: 5 sec
Cumulative number of tunes: 5 times
Measurement range: 400 to 1800 cm$^{-1}$ (Raman drift)
Error: ±2 cm$^{-1}$ Compounds described with document names, etc., indicate that the compounds were produced in accordance with the documents, etc.

Moreover, the abbreviations used in the present specification are well-known and common to a person skilled in the art. In the present specification, the following abbreviations are used.
DMSO: dimethylsulfoxide
IPA: isopropanol
n-: normal
TEA: triethylamine
THF: tetrahydrofuran
$^1$H-NMR: proton nuclear magnetic resonance spectrometry
MS: mass spectrometry The tam "room temperature" in the following Examples and Reference Examples generally refers to about 10° C. to about 35° C. % refers to weight percent unless otherwise specified.

Chemical shifts of proton nuclear magnetic resonance spectra are denoted in δ-unit (ppm) relative to tetramethylsilane, and coupling constants are recorded in Hertz (Hz). The abbreviations of splitting patterns are as follows.
s: singlet, d: doublet, t: triplet, q: quartet, m: multiplet, br.s: broad singlet.

In the reactions using a microwave reactor in the Reference Examples, Initiator™ or Initiator+™ produced by Biotage was used.

Regarding chromatography, as silica gel, Silica Gel60 produced by Merck (70-230 mesh ASTM) or PSQ60B produced by Fuji Silysia Chemical Ltd. was used, or a pre-packed column {column: Hi-Flash™ Column (Silicagel) produced by YAMAZEN, size: one of S (16×60 mm), M (20×75 mm), L (26×100 mm), 2 L (26×150 mm) and 3 L (46×130 mm); or Biotage™ SNAP Ultra Silica Cartridge produced by Biotage, size: one of 10 g, 25 g and 50 g} was used.

As NH silica gel, CHROMATOREX NH-DM2035 produced by Fuji Silysia Chemical Ltd. was used, or a prepacked column {column: Hi-Flash™ Column (Amino) produced YAMAZEN, size: one of S (16×60 mm), M (20×75 mm), L (26×100 mm), 2 L (26×150 mm) and 3 L (46×130 or Presep™ (Luer Lock) NH2(HC) produced by Wako Pure Chemical Industries, Ltd., size: one of type M (14 g/25 mL), type L (34 g/70 mL), type 2 L (50 g/100 mL) and type 3 L (110 g/200 mL)} was used.

As neutral alumina, Aluminum oxide 90 active neutral, 70-230 mesh, Merck, E6NXX was used.

As names of the compounds shown below, except for generally used reagents, those shown in the "E-Notebook" Version 12 (PerkinElmer) were used.

Reference Example 1

Synthesis of 5,10-dimethyl-5,6,9,10,11,12-hexahydropyrido[4″,3″:4′,5′]thieno[2′,3′:4,5]pyrimido[1,2-a]thieno[3,2-f][1,4]diazepine-4,13-dime (hereinafter referred to as "the compound (I)")

19

-continued

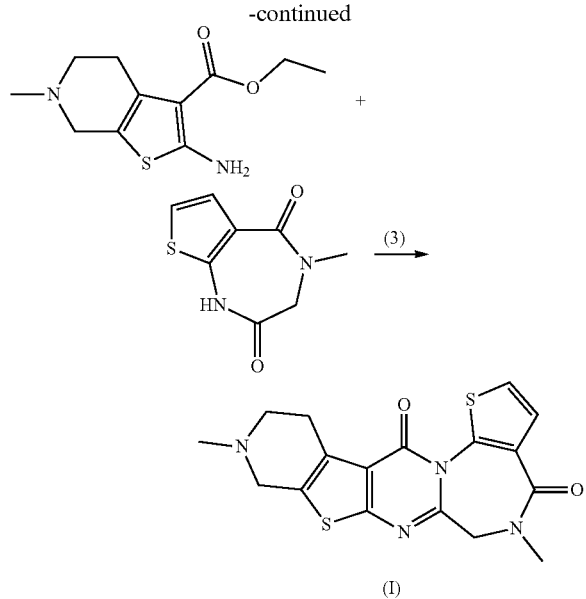

(1) Synthesis of ethyl 2-amino-6-methyl-4,5,6,7-tetrahydrothieno[2,3-c]pyridine-3-carboxylate TEA (61.6 mL, 442 mmol) was added at room temperature to a mixture of 1-methyl-4-piperidone (CAS No. 1445-73-4) (51.5 mL, 442 mmol), ethyl cyanoacetate (CAS No. 105-56-6) (47.2 mL, 442 mmol), sulfur (CAS No. 7704-34-9) (14.2 g, 4.42 mmol) and ethanol (800 mL). The reaction mixture was stirred at 40° C. for 15 hours, and then concentrated under reduced pressure. The residue was purified by column chromatography (NH silica gel, ethyl acetate). The obtained concentrated residue was triturated with ethyl acetate. The precipitates were collected by filtration, washed with ethyl acetate, and dried under reduced pressure to yield the title compound (58.4 g).

$^1$H-NMR (400 MHz, CDCl$_3$) δ (ppm): 1.33 (t, 7.0 Hz, 3H), 2.44 (s, 3H), 2.62-2.70 (m, 2H), 2.79-2.88 (m, 2H), 3.37 (t, J=2.01 Hz, 2H), 4.26 (q, J=7.3 Hz, 2H), 5.97 (br. s, 2H).

MS (ESI) m/z: 241 [M+H]$^+$ (2) Synthesis of 4-methyl-3,4-dihydro-1H-thieno[2,3-e][1,4]diazepine-2,5-dione 1H,2H,4H-Thieno[2,3-d][1,3]oxazine-2,4-dione (CAS No. 103979-54-0) (600 mg, 3.55 mmol) was added to a solution of sarcosine (790 mg, 8.87 mmol) in water (12 mL). The reaction mixture was heated under reflux for 1.5 hours. The reaction mixture was cooled to room temperature. Chloroform was added to the reaction mixture, and the organic layer was separated. The aqueous layer was extracted with chloroform (twice) and ethyl acetate (3 times). The combined organic layer was dried over anhydrous sodium sulfate and filtered, and the filtrate was concentrated under reduced pressure. The obtained solid was dried to yield the title compound (430 mg).

$^1$H-NMR (400 MHz, CDCl$_3$) δ (ppm): 3.23 (s, 3H), 3.99 (s, 2H), 6.90 (d, J=5.9 Hz, 1H), 7.29 (d, J=5.7 Hz, 1H), 8.39 (br. s, 1H).

MS (ESI) m/z: 197 [M+H]$^+$ (3) Synthesis of Compound (I)

Phosphorus oxychloride (1.43 mL, 15.3 mmol) was added at room temperature to a mixture of 4-methyl-3,4-dihydro-1H-thieno[2,3-e][1,4]diazepine-2,5-dione (1.00 g, 5.10 mmol) obtained in step (2), ethyl 2-amino-6-methyl-4,5,6,7-tetrahydrothieno[2,3-c]pyridine-3-carboxylate g, 7.64 mmol) Obtained in step (1), and 1,4-dioxane (30 mL). The reaction mixture was stirred at room temperature for 5 minutes, and stirred at 90° C. for 2 hours. Sodium ethoxide (a 20% solution in ethanol, 21.7 mL, 56.1 mmol) was added over 5 minutes to the reaction mixture cooled to room temperature. The reaction mixture was stirred at room temperature for 1.5 hours, Ethyl acetate, a saturated sodium hydrogen carbonate aqueous solution, and water were sequentially added to the reaction mixture, and the organic layer was separated. The aqueous layer was extracted with ethyl acetate. The combined organic layer was dried over anhydrous magnesium sulfate and filtered, and the filtrate was concentrated under reduced pressure. The residue was purified by column chromatography (silica gel, 20%-50% methanol/ethyl acetate). The obtained solid was triturated with ethanol, and the precipitates were collected by filtration. The obtained solid was washed with ethanol, and dried under reduced pressure to yield the title compound (712 mg).

$^1$H-NMR. (400 MHz, CDCl$_3$) δ (ppm): 2.52 (s, 3H), 2.71-2.87 (m, 2H), 3.05-3.30 (m, 5H), 3.59-3.75 (m, 2H), 4.23 (d, of =14.8 Hz, 1H), 4.57 (d, J=14.8 Hz, 1H), 7.35 (d, J=6.2 Hz, 1H), 7.39 (d, J=5.9 Hz, 1H).

MS (ESI) m/z: 373 [M+H]$^+$

Example 1

Preparation of Crystal of Compound (I)

To 1.5 L of 0.3 M hydrochloric acid, 152.08 g of the compound (I) was added, and 450 ml of ethyl acetate was added to this solution, followed by stirring for 5 minutes. The aqueous layer was separated and washed with 450 ml of ethyl acetate, and the insoluble matter was removed by filtration. To the filtrate, 100 ml of a 1 N aqueous solution of sodium hydroxide was added in a water bath at 20° C. and the mixture was stirred for 15 minutes. To the mixture, 350 ml of a 1 N aqueous solution of sodium hydroxide was added and the obtained suspension was stirred for 2 hours 30 minutes. The resulting crystal was collected by filtration, washed sequentially with 300 ml, 450 nil, and 300 ml of water, 300 nil, 350 nil, and 300 ml of ethanol, and dried under reduced pressure to yield 141.7 g of the title crystal. Powder X-ray diffraction peak (reflection method, 2θ±0.2°): 9.0°, 11.1°, 18.1°, 21.9°, 23.6°, 24.4°, 24.9°, 28.5°

The powder X-ray diffraction pattern of the crystal of the compound (I) obtained by the above-mentioned method is shown in FIG. 1.

Example 2

Preparation of A-Type Crystal of Compound (I) Monohydrochloride

Into a screw-top test tube, 101 mg of the compound (I) was added. Thereinto, 0.2 mL of 1.5 M hydrochloric acid was added and dissolved, Thereinto, 1.8 mL of IPA was added, irradiated with ultrasonic waves, and then stirred with a stirrer at 40° C. for one day. After stirring at room temperature for further 1 hour, the sample was collected by filtration by using a filter (0.2 μm), rinsed with 0.5 mL of IPA/water (9/1, v/v), and air-dried under a nitrogen stream. The residue was dried at 70° C. for about 1 hour to yield the title crystal (103 mg).

Powder X-ray diffraction peaks (transmission method, 2θ±0.2°): 6.1°, 7.8°, 11.6°, 16.2°, 19.9°, 20.8°, 25.2°, 25.7°, 26.9°, 29.9°

$^{13}$C-NMR (100 MHz, solid state) δ (ppm): 164.0, 162.5, 160.5, 153.9, 151.6, 150.7, 133.6, 131.1, 129.6, 128.4, 126.9, 125.2, 123.7, 121.3, 120.3, 119.5, 53.7, 52.0, 50.9, 44.7, 36.5, 22.6

Raman shift peaks (cm$^{-1}$): 409, 587, 763, 976, 1428, 1493, 1688

Figure 2:
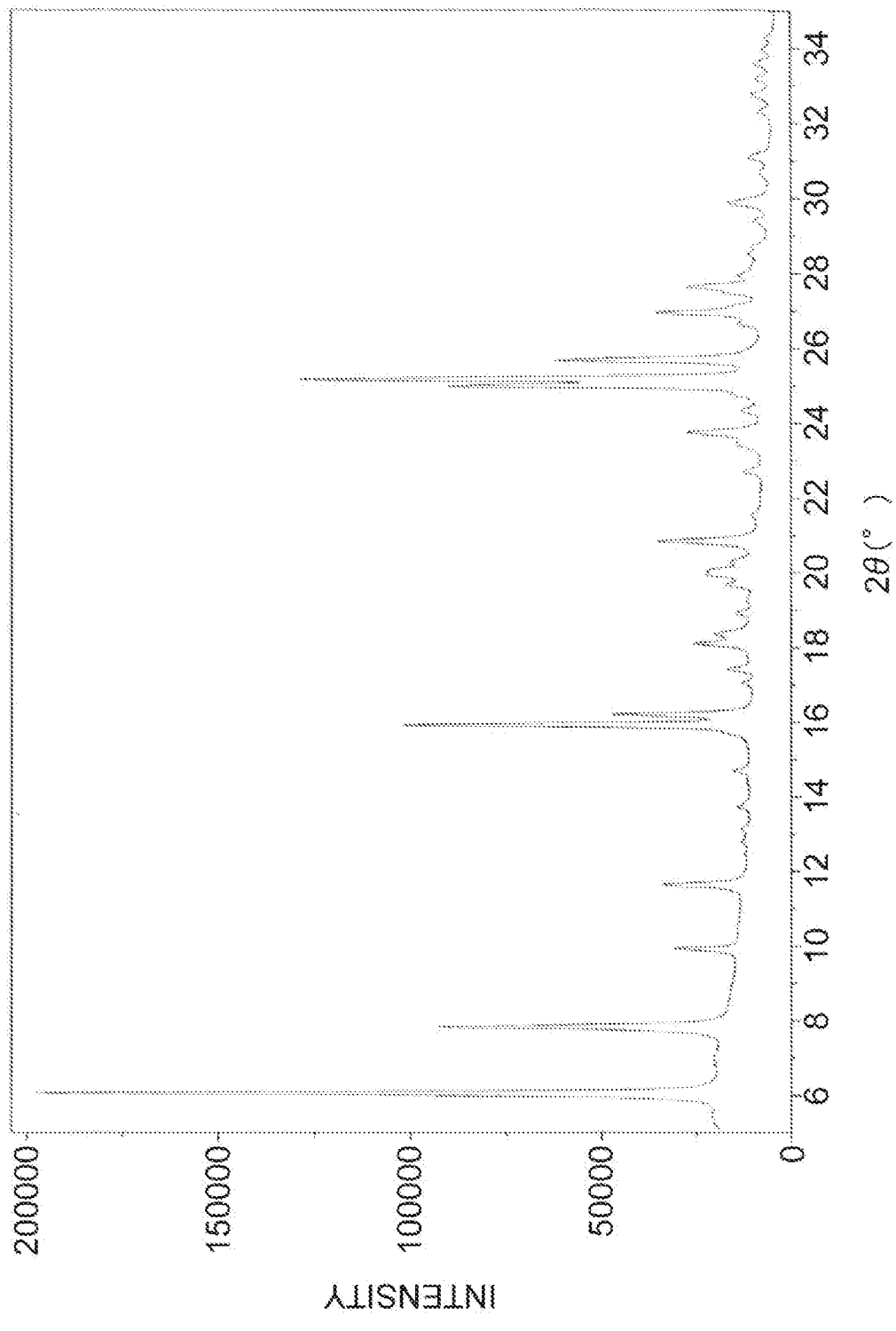
FIG. 2 is a powder X-ray diffraction pattern of the A-type crystal of the compound (I) monohydrochloride obtained in Example 2. The abscissa represents the diffraction angle (2θ) and the ordinate represents the peak intensity
Figure 9:
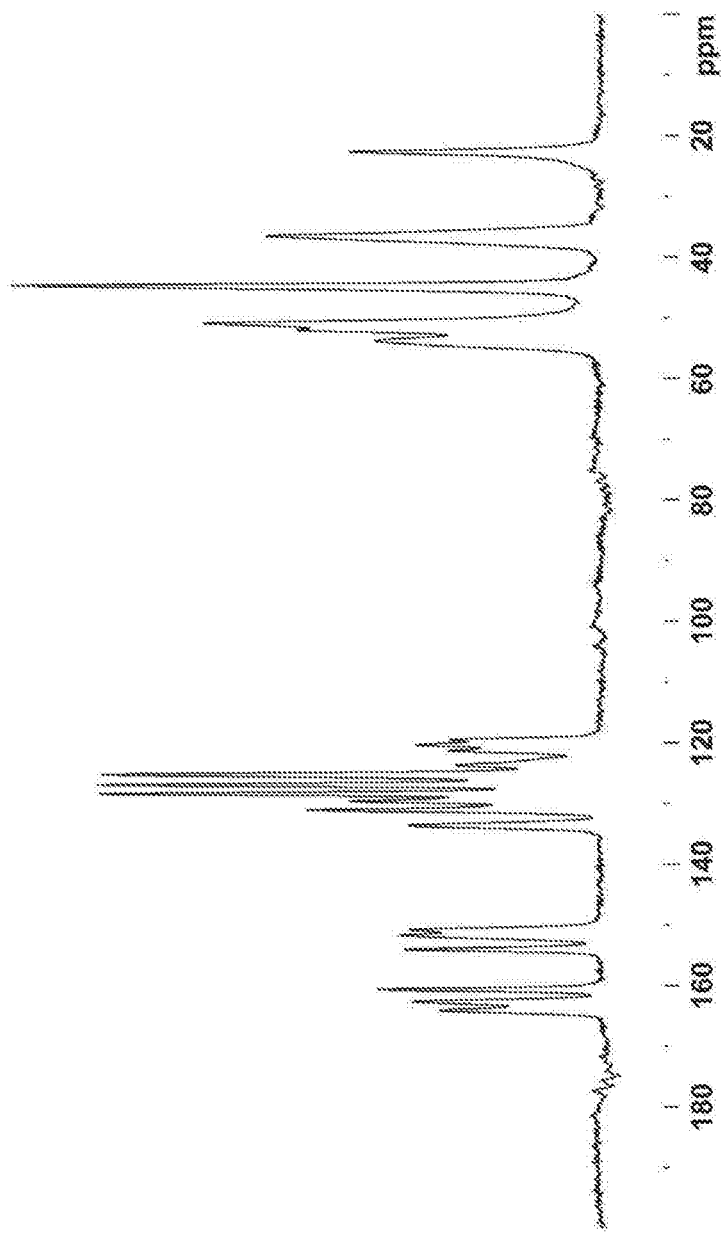
FIG. 9 is a $^{13}C$ solid state NMR spectrum of the A-type crystal of the compound (I) monohydrochloride obtained in Example 2. The abscissa represents the chemical shift (δ) and the ordinate represents the peak intensity.
Figure 12:
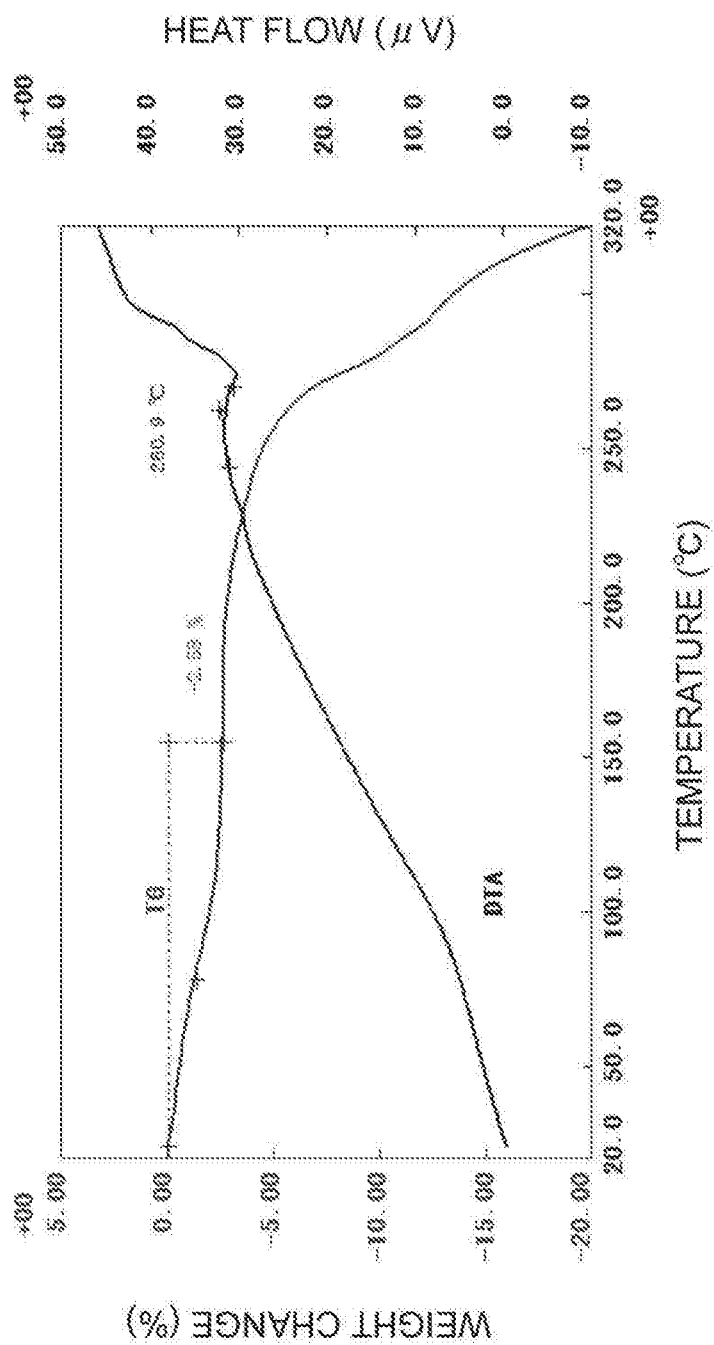
FIG. 12 is a thermal analysis TG-DTA chart of the A-type crystal of the compound (I) monohydrochloride Obtained in Example 2. The abscissa represents the temperature, the left ordinate represents the weight change of TG, and the right ordinate represents the heat flow of DTA.

The powder X-ray diffraction pattern of the A-type crystal of the compound (I) monohydrochloride obtained by the above-mentioned method is shown in FIG. 2, the $^{13}$C solid state NMR spectrum is shown in FIG. 9, the thermal analysis TG-DTA chart is shown in FIG. 12, and the Raman spectrum is shown in FIG. 19.

Example 3

Preparation of C-Type Crystal of Compound (I) Monohydrochloride

Into a screw-top test tube, 1020 mg of the compound (I) was added. In 20 mL of methanol, 1.5 equivalent of hydrochloric acid (353 μL) was dissolved and this solution was added to the sample. The sample was stirred with a stirrer at room temperature for 2 days. The sample was collected by filtration with a filter (0.2 μm). The obtained solid was dried under reduced pressure for about 2 hours, then dried at 70° C. for 1 hour to yield the title crystal (1048 mg).

Powder X-ray diffraction peak (transmission method, 2θ±0.2°): 6.0°, 7.7°, 9.7°, 11.4°, 15.8°, 16.9°, 18.1°, 23.2°, 25.4°, 27.6°

$^{13}$C-NMR (100 MHz, solid state) δ (ppm): 162.5, 160.5, 159.6, 153.8, 151.1, 134.1, 131.6, 128.4, 127.6, 125.6, 120.0, 54.0, 52.6, 50.9, 44.3, 43.5, 38.9, 32.3, 22.4

Figure 4:
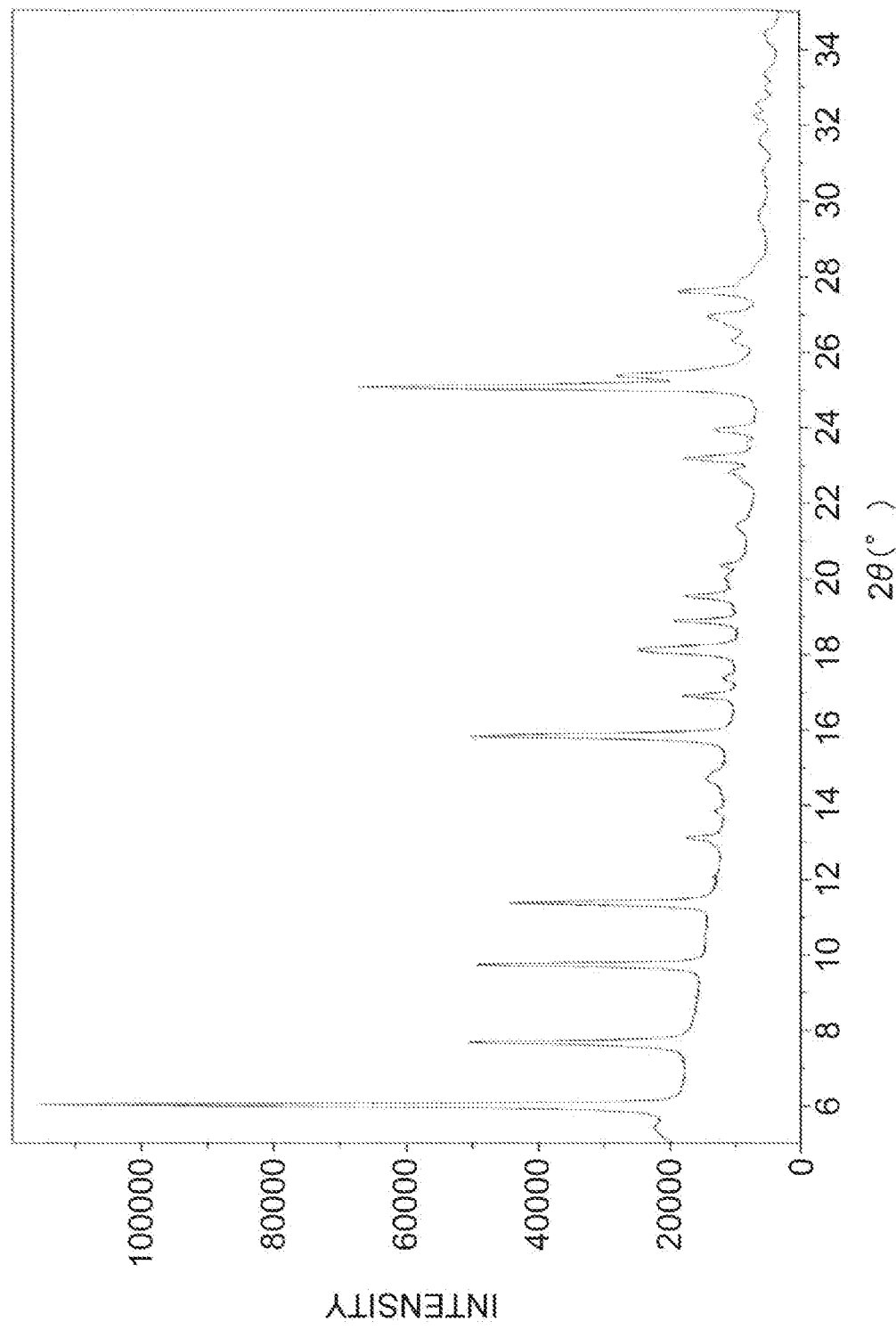
FIG. 4 is a powder X-ray diffraction pattern of the C-type crystal of the compound (I) monohydrochloride obtained in Example 3. The abscissa represents the diffraction angle (2θ) and the ordinate represents the peak intensity.
Figure 11:
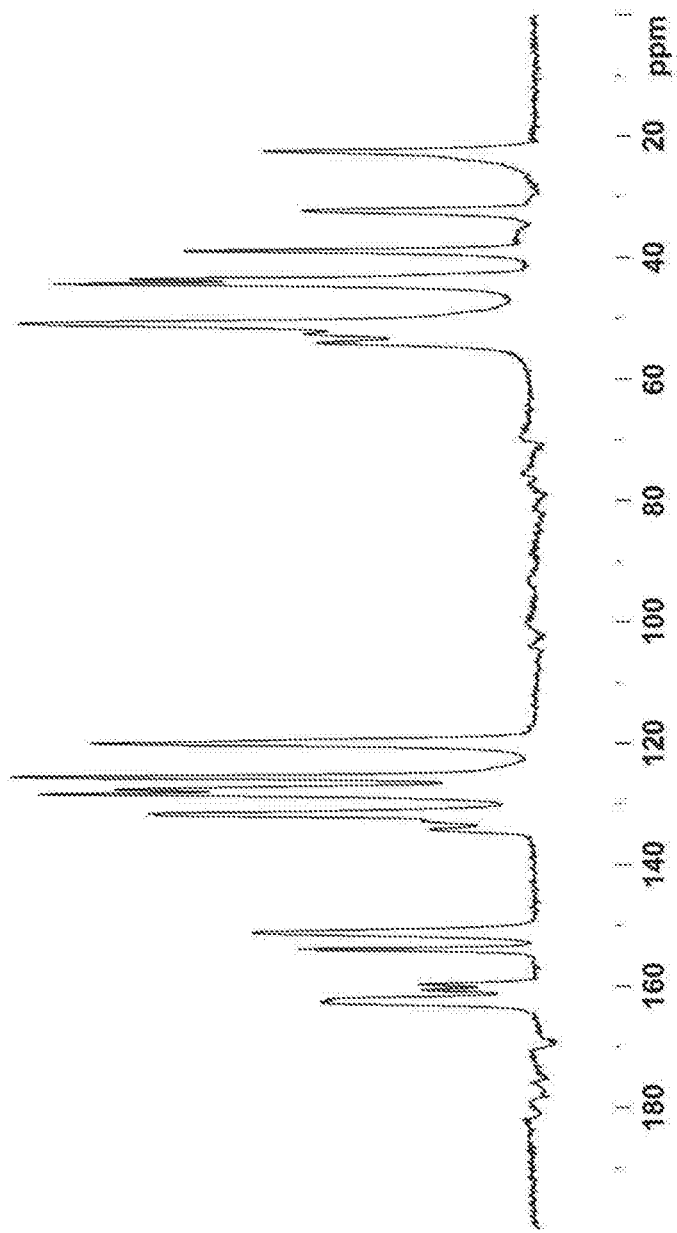
FIG. 11 is a $^{13}C$ solid state NMR spectrum of the C-type crystal of the compound (I) monohydrochloride obtained in Example 3. The abscissa represents the chemical shift (δ) and the ordinate represents the peak intensity.
Figure 14:
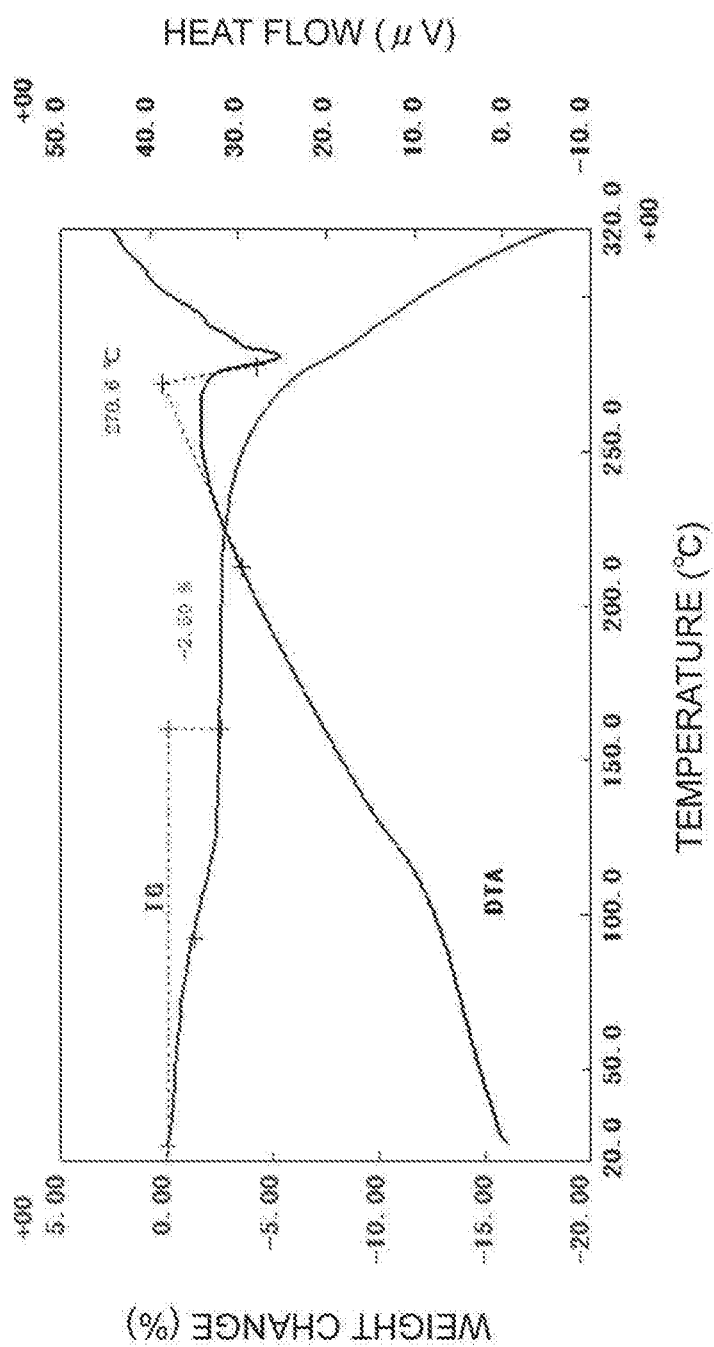
FIG. 14 is a thermal analysis TG-DTA, chart of the C-type crystal of the compound (I) monohydrochloride obtained in Example 3. The abscissa represents the temperature, the left ordinate represents the weight change of TG, and the right ordinate represents the heat flow of DTA.

The powder X-ray diffraction pattern of the C-type crystal of the compound (I) monohydrochloride obtained by the above-mentioned method is shown in FIG. 4, the $^{13}$C solid state NMR spectrum is shown in FIG. 11, and the thermal analysis TG-DTA chart is shown in FIG. 14.

Example 4

Preparation of B-Type Crystal of Compound (I) Monohydrochloride

Into a platinum crucible, 303 mg of the hydrochloride crystal obtained in Example 3 was added and heated at 160° C. for 15 minutes to yield the title crystal (293 mg).

Powder X-ray diffraction peak (transmission method, 2θ±0.2°): 6.3°, 9.7°, 10.1°, 17.9°, 19.0°, 19.4°, 23.4°, 26.3°, 27.3°, 32.0°

$^{13}$C-NMR. (100 MHz, solid state) δ (ppm): 162.0, 160.1, 153.8, 151.1, 133.4, 130.7, 128.3, 126.9, 125.6, 120.3, 51.2, 43.6, 32.3, 22.3

Figure 3:
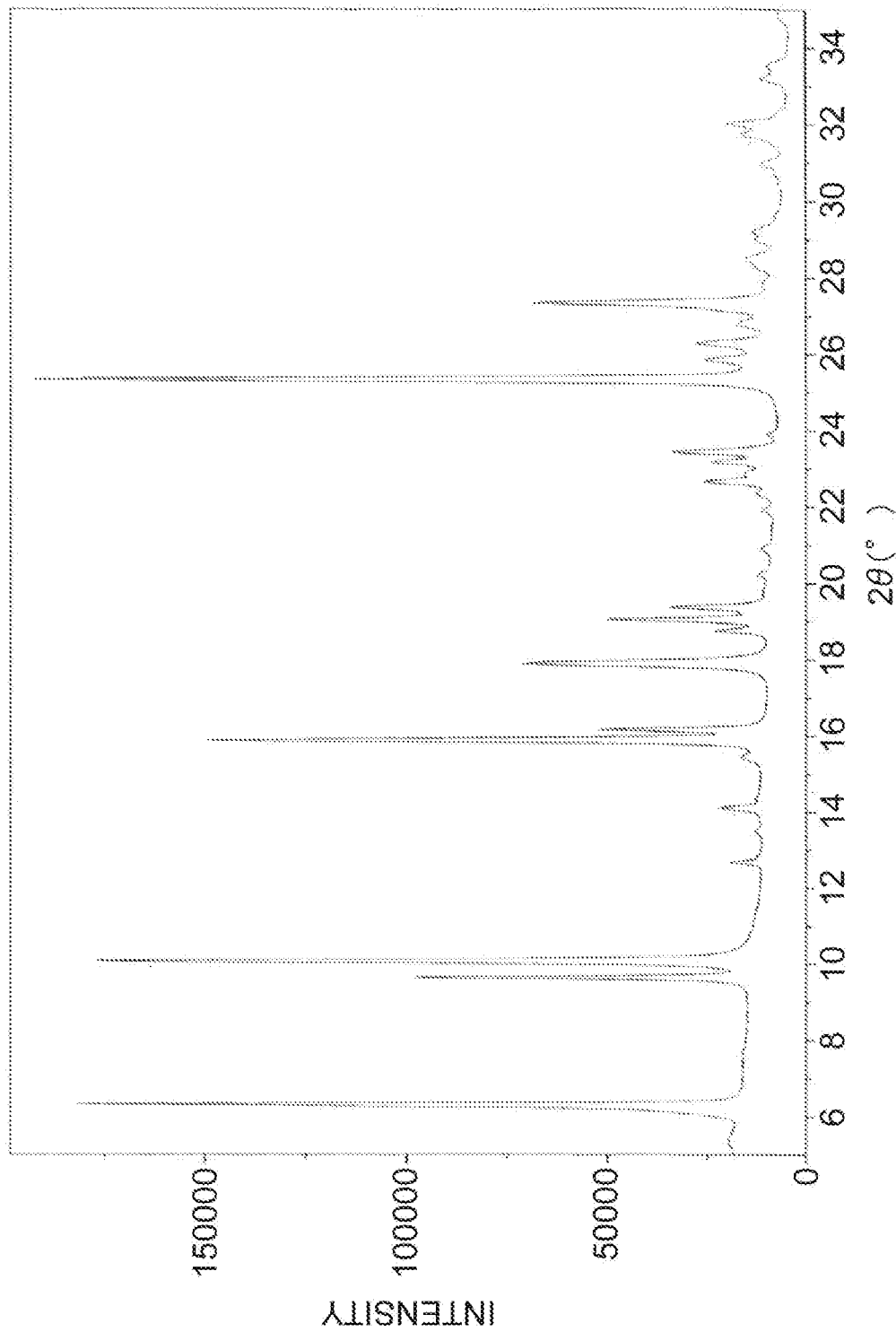
FIG. 3 is a powder X-ray diffraction pattern of the B-type crystal of the compound (I) monohydrochloride obtained in Example 4. The abscissa represents the diffraction angle (2θ) and the ordinate represents the peak intensity.
Figure 10:
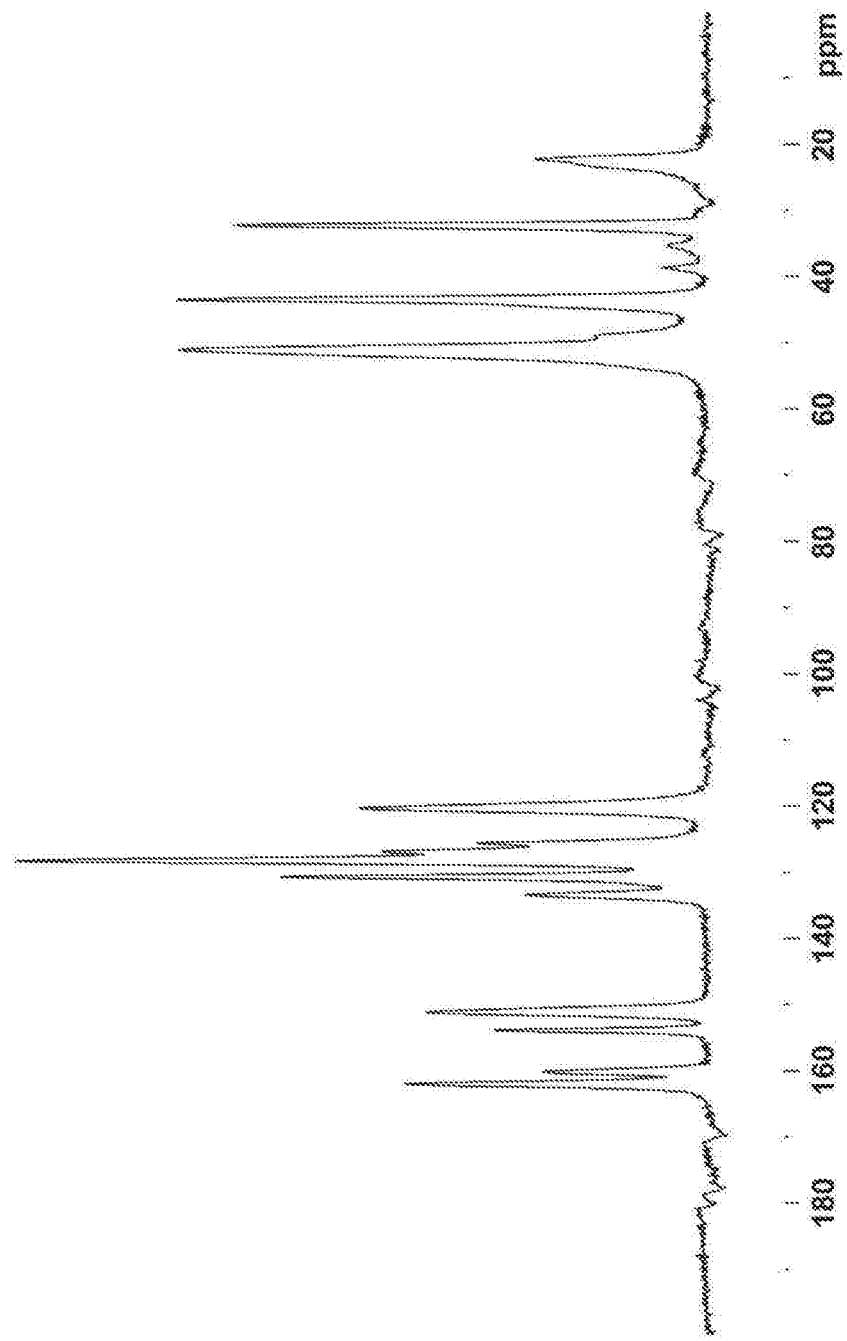
FIG. 10 is a $^{13}C$ solid state NMR spectrum of the B-type crystal of the compound (I) monohydrochloride obtained in Example 4. The abscissa represents the Chemical shift (δ) and the ordinate represents the peak intensity.
Figure 13:
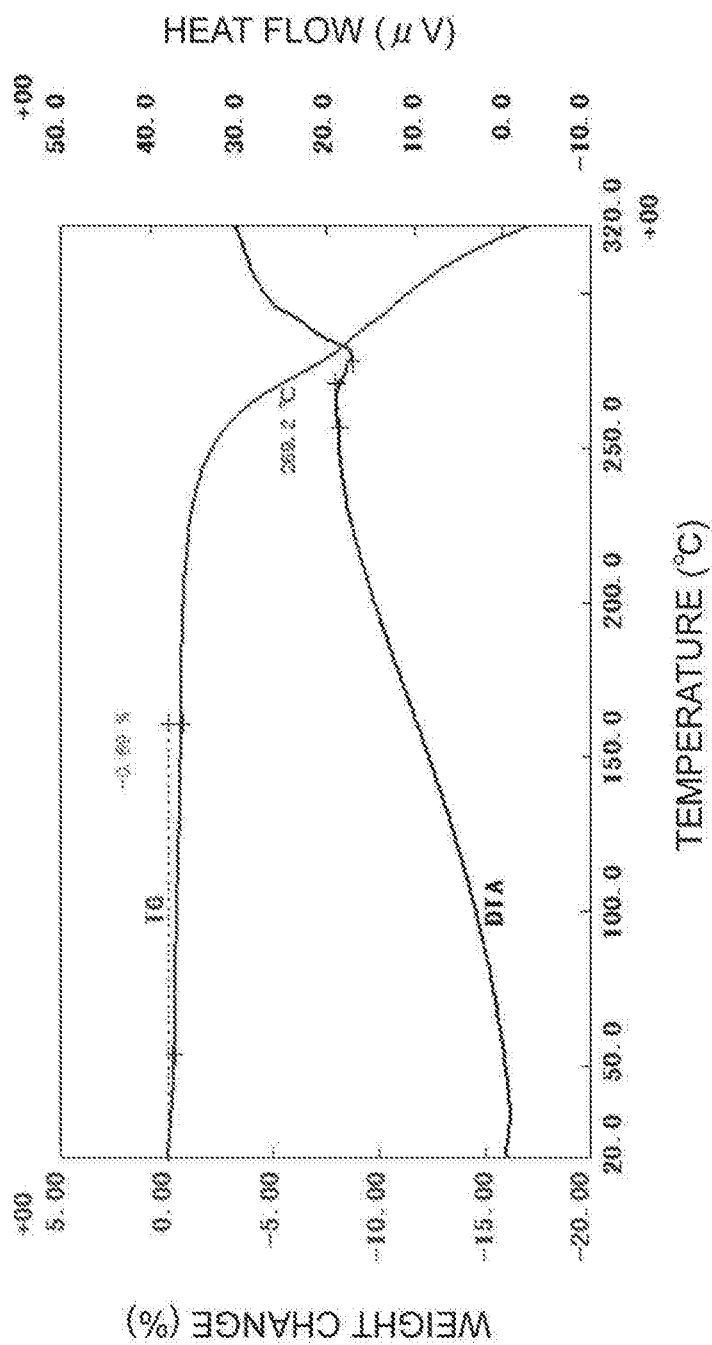
FIG. 13 is a thermal analysis TG-DTA chart of the B-type crystal of the compound (I) monohydrochloride obtained in Example 4. The abscissa represents the temperature, the left ordinate represents the weight change of TG, and the right ordinate represents the heat flow of DTA.

The powder X-ray diffraction pattern of the B-type crystal of the compound (I) monohydrochloride obtained by the above-mentioned method is shown in FIG. 3, the $^{13}$C, solid state NMR spectrum is shown in FIG. 10, and the thermal analysis TG-DTA chart is shown in FIG. 13.

Example 5

Preparation of D-Type Crystal of Compound (I) Monohydrochloride

Into a screw-top test tube, 227 mg of the mixture of the hydrochloride crystals obtained in Examples 2 and 3, and 8 mL of ethanol were added. The mixture was stirred with a stirrer at 65° C. After about 1 hour, the mixture was irradiated with ultrasonic waves and stirred at the same temperature for one day. The sample was collected by filtration with a filter (0.2 μm) to yield the title crystal (203 mg).

Powder X-ray diffraction peak (transmission method, 2θ±0.2°): 6.6°, 14.6°, 16.1°, 20.5°, 21.0°, 23.0°, 24.5°, 26.4°, 28.0°, 32.5°

Figure 5:
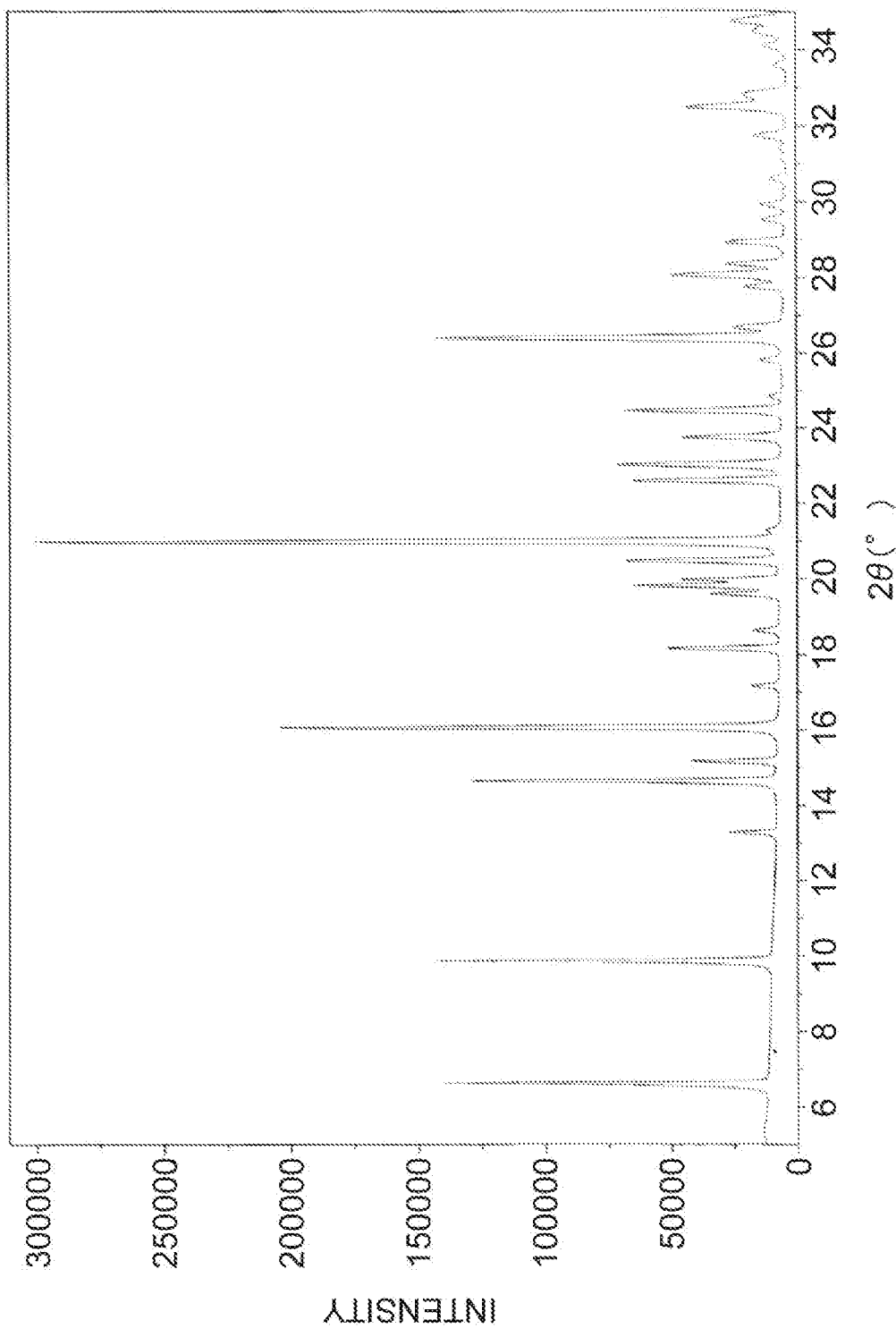
FIG. 5 is a powder X-ray diffraction pattern of the D-type crystal of the compound (I) monohydrochloride obtained in Example 5. The abscissa represents the diffraction angle (2θ) and the ordinate represents the peak intensity.
Figure 15:
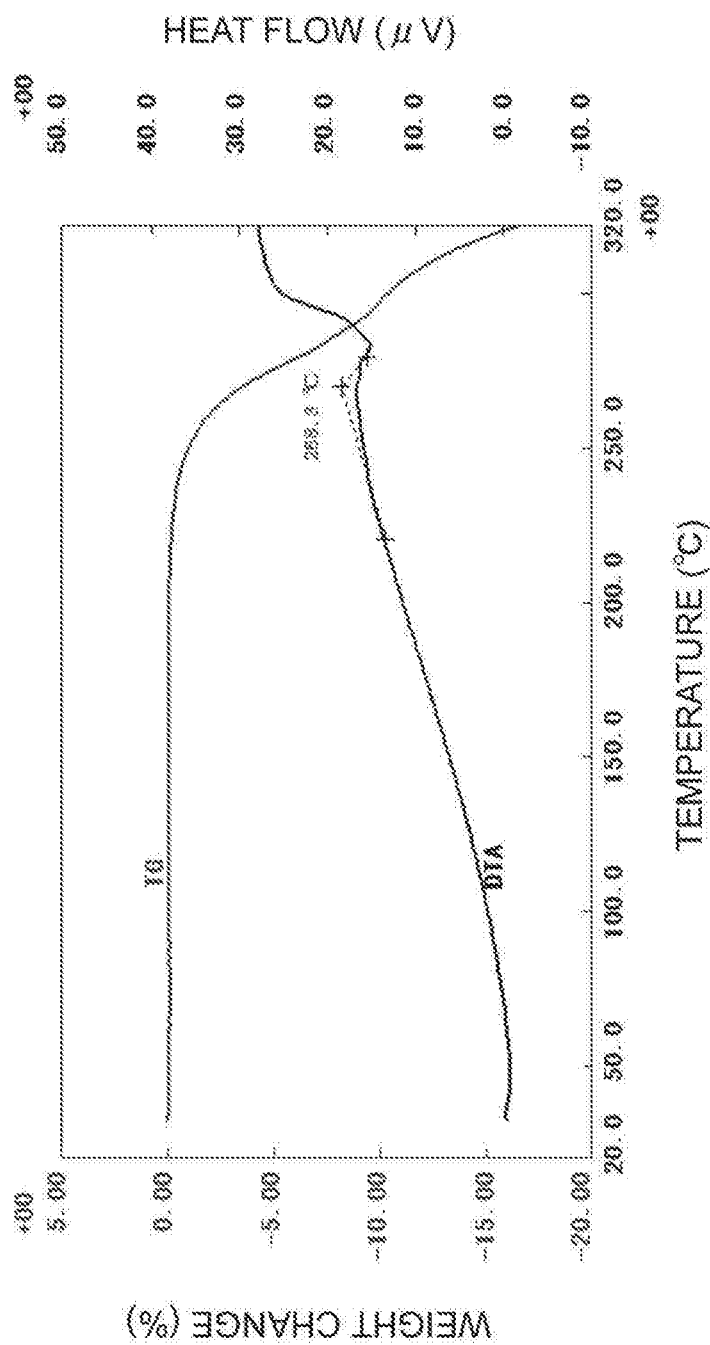
FIG. 15 is a thermal analysis TG-DTA chart of the D-type crystal of the compound (I) monohydrochloride obtained in Example 5. The abscissa represents the temperature, the left ordinate represents the weight change of TG, and the right ordinate represents the heat flow of DTA.

The powder X-ray diffraction pattern of the D-type crystal of the compound (I) monohydrochloride obtained by the above-mentioned method is shown in FIG. 5 and the thermal analysis TG-DTA chart is shown in FIG. 15.

Example 6

Preparation of E-Type Crystal of Compound (I) Monohydrochloride

Into a screw-top test tube, 108 mg of the hydrochloride crystal obtained in Example 2 and 5 mL of acetonitrile were added. The mixture was stirred with a stirrer at 60° C. for one day and the sample was collected by filtration with a filter (0.2 μm). The obtained solid and 5 mL of acetonitrile were added into the screw-top test tube again and stirred with a stirrer at 60° C. for one day. The sample was collected by filtration with a filter (0.2 μm) under a nitrogen stream to yield the title crystal (89.7 mg).

Powder X-ray diffraction peak (transmission method, 2θ±0.2°): 6.4°, 11.3°, 15.7°, 18.0°, 19.2°, 22.8°, 24.6°, 25.4°, 26.0°, 27.3°

Figure 6:
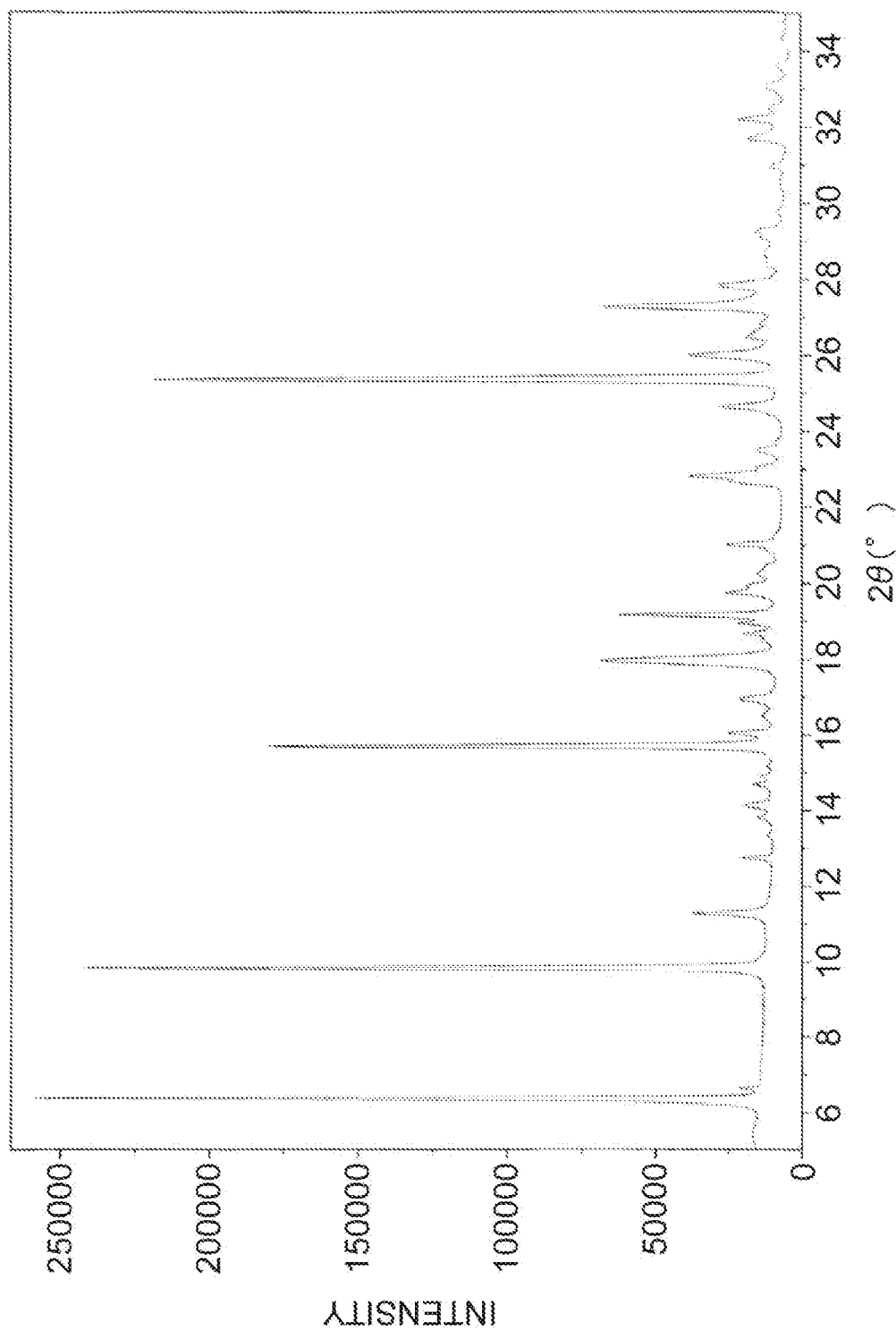
FIG. 6 is a powder X-ray diffraction pattern of the E-type crystal of the compound (I) monohydrochloride obtained in Example 6. The abscissa represents the diffraction angle (2θ) and the ordinate represents the peak intensity.
Figure 16:
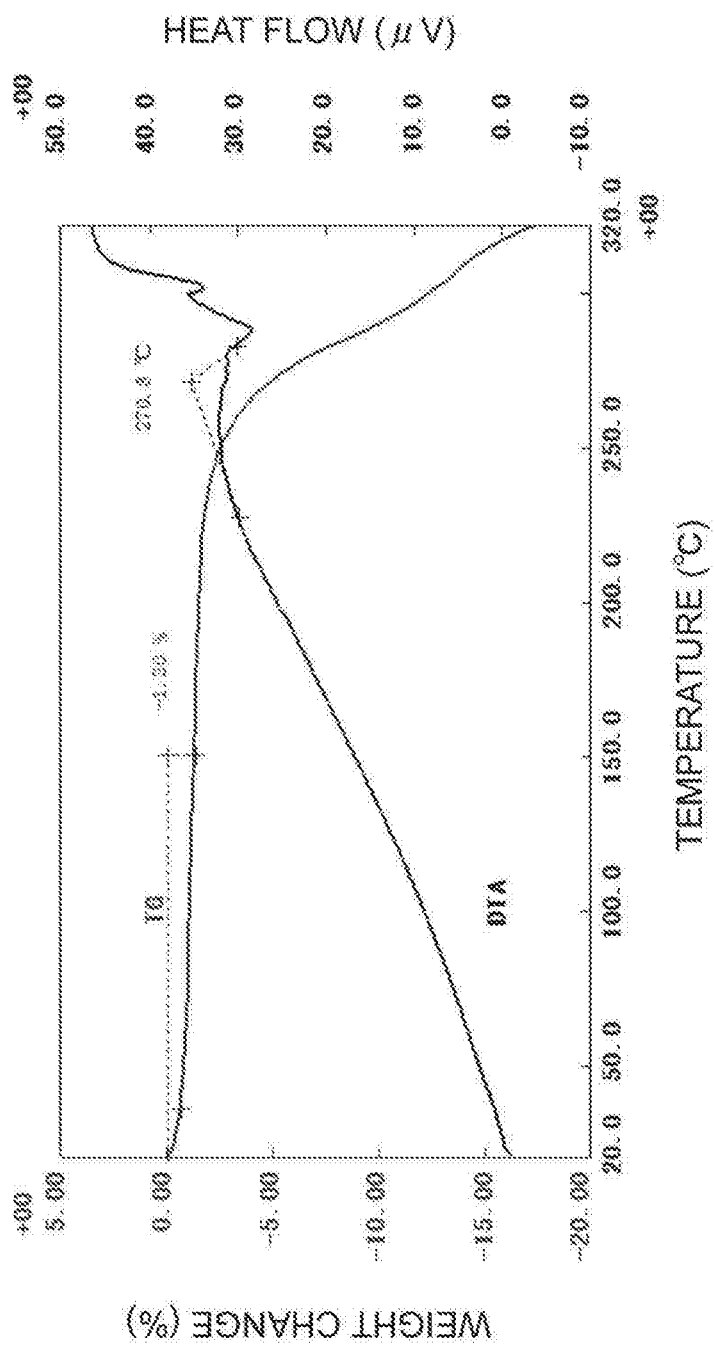
FIG. 16 is a thermal analysis TG-DTA chart of the E-type crystal of the compound (I) monohydrochloride Obtained in Example 6. The abscissa represents the temperature, the left ordinate represents the weight change of TG, and the right ordinate represents the heat flow of DTA.

The powder X-ray diffraction pattern of the E-type crystal of the compound (f) monohydrochloride obtained by the above-mentioned method is shown in FIG. 6 and the thermal analysis TG-DTA chart is shown in FIG. 16.

Example 7

Preparation of F-Type Crystal of Compound (I) Monohydrochloride

Into a screw-top test tube, 101 mg of the hydrochloride crystal obtained in Example 2 and 5 mL of ethanol were added. The mixture was stirred with a stirrer at 60° C. for one day. The sample was collected by filtration with a filter (0.2 μm). The obtained solid and 5 mL of ethanol were added into the screw-top test tube again and stirred with a stirrer at 60° C. for 4 hours. The sample was collected by filtration with a filter (0.2 μm) to yield the title crystal (75.0 mg).

Powder X-ray diffraction peak (transmission method, 2θ±5.9°, 7.3°, 9.3°, 10.7°, 13.8°, 15.6°, 16.4°, 18.7°, 25.1°, 26.8°

Figure 7:
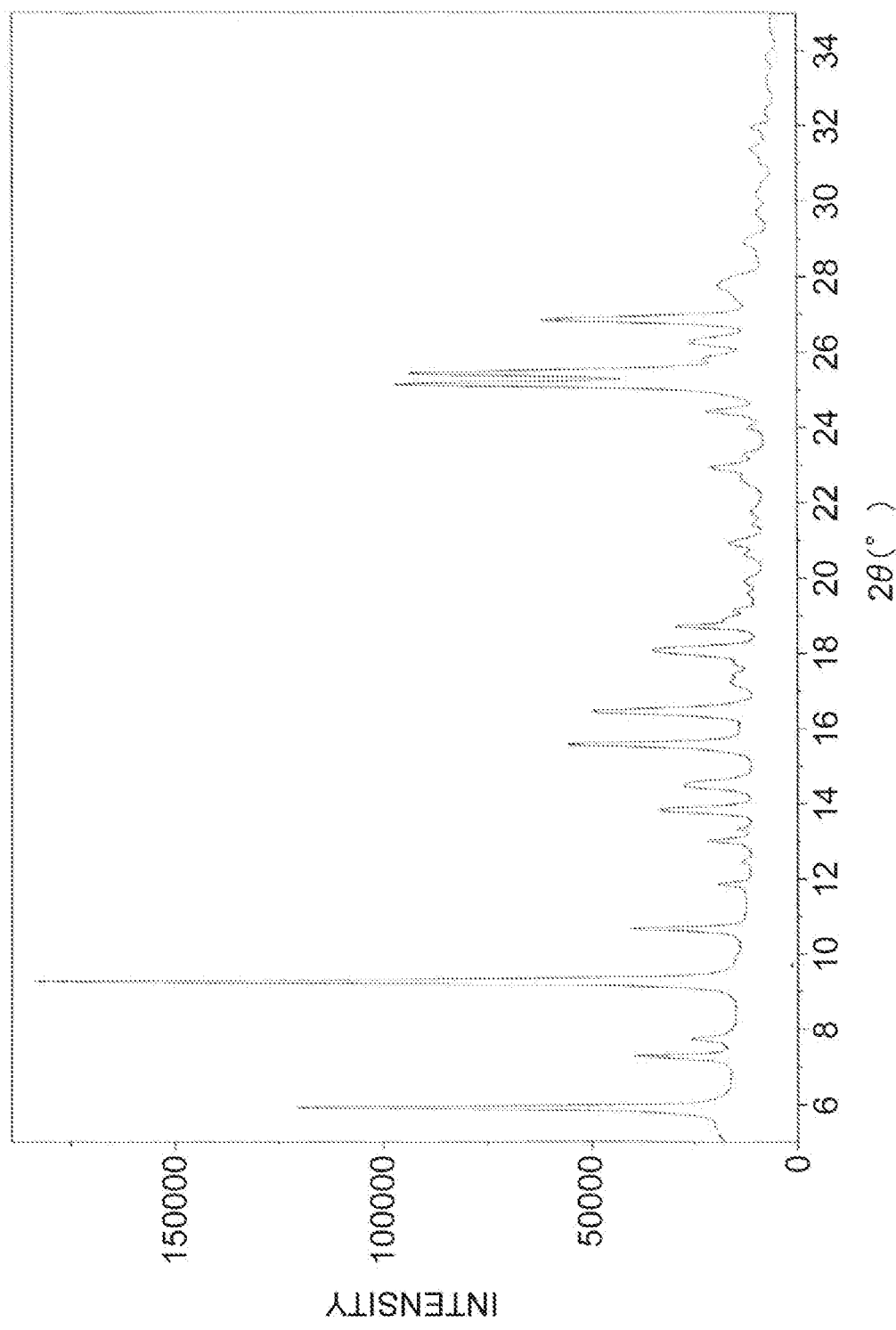
FIG. 7 is a powder X-ray diffraction pattern of the E-type crystal of the compound (I) monohydrochloride obtained in Example 7. The abscissa represents the diffraction angle (2θ) and the ordinate represents the peak intensity.
Figure 17:
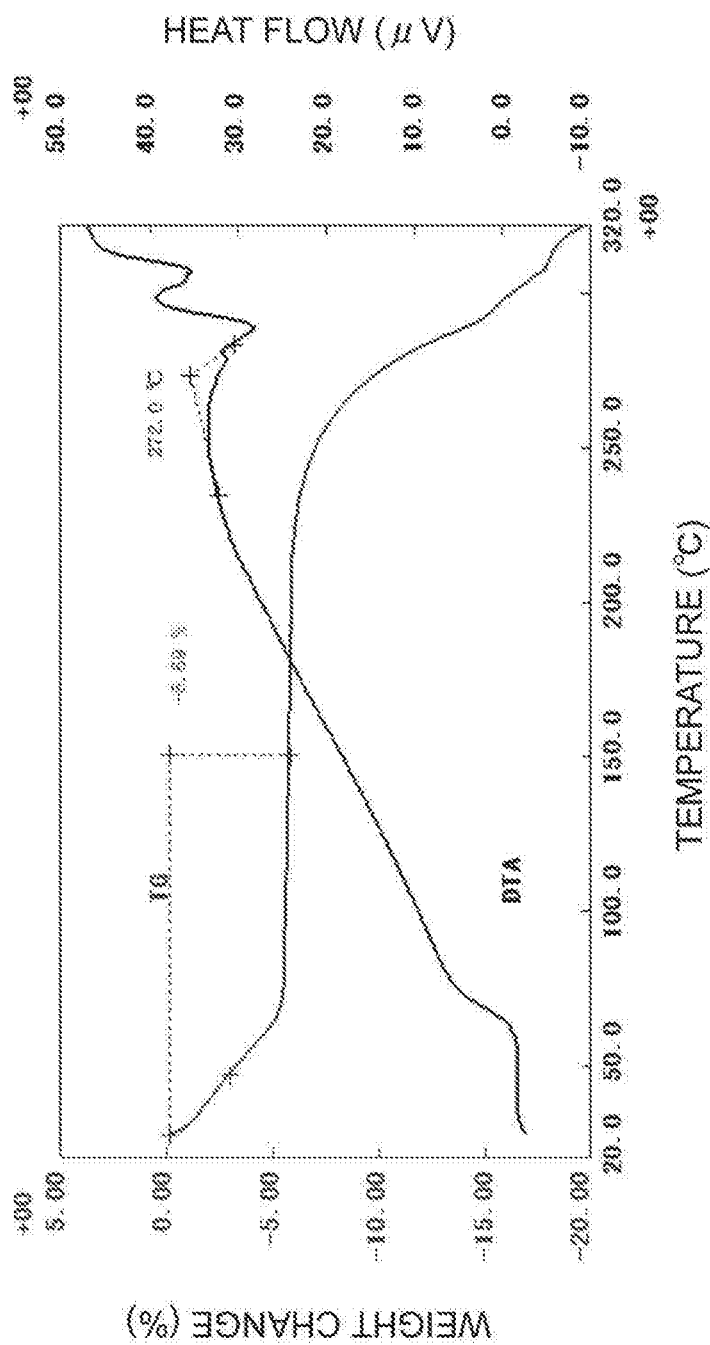
FIG. 17 is a thermal analysis TG-DTA chart of the F-type crystal of the compound (I) monohydrochloride obtained in Example 7. The abscissa represents the temperature, the left ordinate represents the weight change of TG, and the right ordinate represents the heat flow of DTA.

The powder X-ray diffraction pattern of the F-type crystal of the compound (I) monohydrochloride obtained by the above-mentioned method is Shown in FIG. 7 and the thermal analysis TG-DTA chart is shown in FIG. 17.

Example 8

Preparation of Crystal of Compound (I) Monohydrobromide

Into a screw-top test tube, 933 mg of the compound (I) was added. Into 20 mL of methanol, 1.5 equivalent (434 μL) of hydrobromic acid was dissolved and this solution was added to the sample. The mixture was stirred with a stirrer at room temperature for 3 days. The sample was collected by filtration with a filter (0.2 μm) and dried at 60° C. for 1 hour to yield the title crystal (1111 mg).

Powder X-ray diffraction peak (transmission method, 2θ±0.2°): 6.0°, 7.8°, 10.0°, 11.7°, 17.8°, 20.8°, 23.5°, 24.5°, 25.2°, 27.3°

Figure 8:
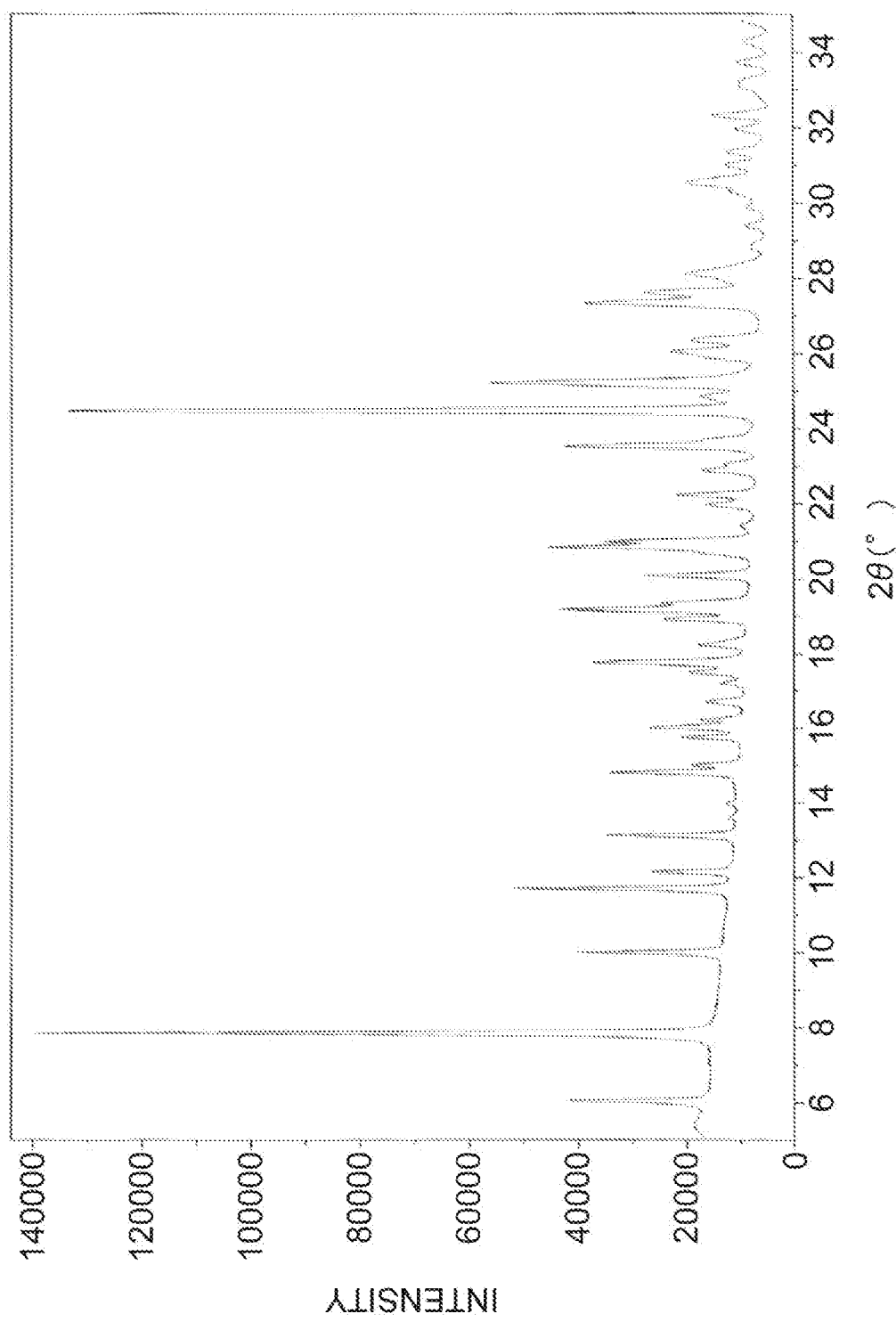
FIG. 8 is a powder X-ray diffraction pattern of the crystal of the compound (I) monohydrobromide obtained in Example 8. The abscissa represents the diffraction angle (2θ) and the ordinate represents the peak intensity.
Figure 18:
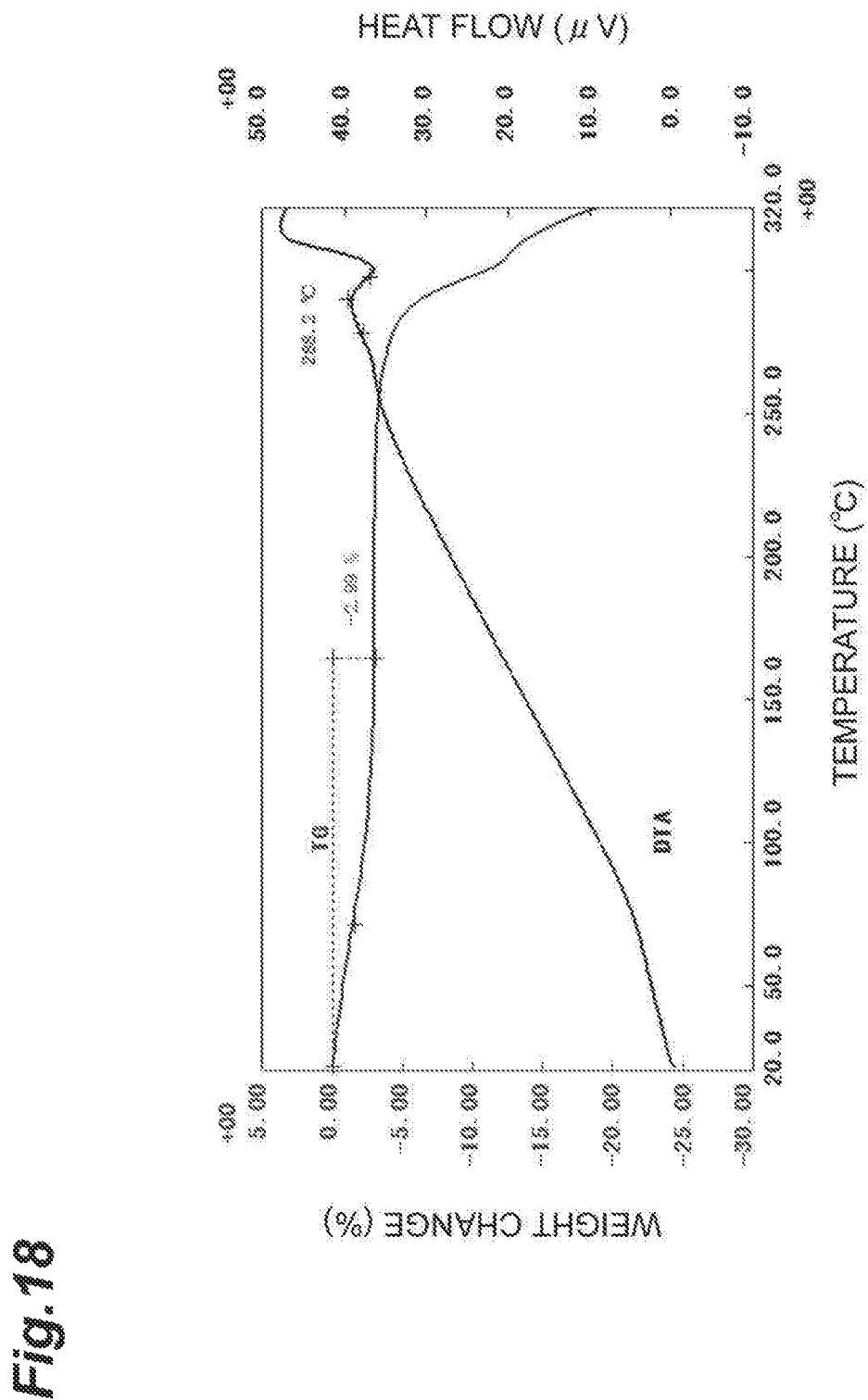
FIG. 18 is a thermal analysis TG-DTA chart of the crystal of the compound (I) monohydrobromide obtained in Example 8. The abscissa, represents the temperature, the left ordinate represents the weight change of TG, and the right ordinate represents the heat flow of DTA.

The powder X-ray diffraction pattern of the compound (I) monohydrobromide obtained by the above-mentioned method is shown in FIG. 8 and the thermal analysis TG-DTA chart is shown in FIG. 18.

Pharmacological Test Examples

Measurement of Acetylcholine (ACh) Release in the Rat Primary Septal Neuron Culture System in the Presence of NGF
(1) Rat Primary Septal Neuron Culture The septal area was isolated from Sprague-Dawley (SD) rats (Charles River Laboratories Japan, Inc.) at a fetal age of 18 days, and cultured. Specifically, fetuses were aseptically removed from pregnant rats under isoflurane anesthesia. The brain was extracted from each fetus, and immersed in ice-cooled L-15 medium (11415-064. Thermo Fisher Scientific), The septal area was dissected from the extracted brain under a stereoscopic microscope. The dissected septal area was subjected to enzyme treatment in an enzyme solution containing 0.25% trypsin (15050-065. Thermo Fisher Scientific) and 0.01% DNase (D5025-1.50KU, Sigma) at 37° C. for 30 minutes, thereby dispersing the cells. In this case, the enzyme reaction was terminated by adding inactivated horse serum (26050-088. Thermo Fisher Scientific). The enzyme-treated solution was centrifuged at 1000 rpm for 3 minutes, and the supernatant was removed. A medium in an amount of 10 mL was added to the obtained cell mass. The medium used was Dulbecco's Modified Eagles Medium (044-29765, WAKO) supplemented with N2 supplement (17502-048, Thermo Fisher Scientific), 1 mM sodium pyruvate (11360-070, Thermo Fisher Scientific), and Penicillin-Streptomycin (15140-1221, Thermo Fisher Scientific). The cells of the cell mass to which the medium was added were redispersed by gentle pipetting, and then centrifuged again at 1000 rpm for 3 minutes, and the supernatant was removed. The medium in an amount of 10 mL was added to the obtained cell mass, and the cell dispersion was filtered through a 40-μm nylon mesh (Cell Strainer) to remove the cell mass, thereby obtaining a neuronal cell suspension. The neuronal cell suspension was diluted with the medium, and 10% inactivated bovine serum (26140-079, Thermo Fisher Scientific) and 10% inactivated horse serum were added. Thereafter, 100 μL/well of the suspension was seeded in a 96-well plate (354461, CORNING) pre-coated with poly-D-lysine so that the initial culture density was $1.4 \times 10^5$ cells/cm$^2$. After the seeded cells were cultured under 5% $CO_2$-95% air in a 37° C. incubator for 2 days, the entire medium was replaced with 120 μL of fresh medium, and the cells were subsequently cultured for 5 days.
(2) Compound Addition On the 7th day of culture, compound was added in the following manner. A solution of the test compound in DMSO was diluted with the medium so that the concentration was 10 times higher than the final concentration. NGF (450-01, PEPRO TECH, INC.) was prepared at 0.3 ng/mL. These two solutions were added each in an amount of 15 μL/well, and the mixture was mixed well. The final DMSO concentration was 0.1% or less. Moreover, only DMSO and NGF were added to the control group.
(3) ACh Release Measurement One day after compound addition, an amount of ACh release was measured by HPLC in the following manner. A warmed buffer was added at 100 μL/well to the well after the medium was eliminated, and the buffer was immediately removed. Thereafter, a buffer to which 10 μm choline, 10 μm physostigmine, and 6 mM KCl were added was added at 120 μL/well. The buffer was prepared by adding 125 mM NaCl, 25 mM 4-(2-hydroxyethyl)-1-piperazineethanesulfonic acid, 1.2 mM $KH_2PO_4$, 1.2 mM $MgSO_4$, 2.2 mM $CaCl_2$ ($2H_2O$), and 10 mM glucose to sterilized water, and the final pH of the solution was set to 7.4. After the 96-well plate to which the buffer was added was incubated under 5% $CO_2$-95% air in a 37° C. incubator for 40 minutes, 80 μL of buffer was collected. An internal standard solution IPHC ($5 \times 10^{-7}$ M) was added in an amount of 6 μL to the collected buffer, and the buffer was transferred to a tube for HPLC measurement and subjected to HPLC measurement. The results are represented by the effect of each compound as the percentage (% of control) of the ACh concentration in the buffer of the control group, and the compound concentration of Reference Example 1 showing a 20% increase from the ACh concentration in the buffer of the control group was 0.1 μM.

Measurement of Choline Acetyltransferase (ChAT) mRNA Expression Levels in the Rat Septal Area
(1) Compound Administration In this study, SD male rats (Charles River Laboratories Japan, Inc. with a body weight of about 250 to 350 g were used. The compound was dissolved in 0.01 mol/L hydrochloric acid, and orally administered.
(2) Sampling At 24 hours after the administration of the compound, the whole brain tissue was collected under pentobarbital anesthesia. The medial septum was isolated from whole brain on ice and frozen with liquid nitrogen, and them stored at −80° C.
(3) Measurement of ChAT snRNA Expression Levels For RNA purification, RNeasy Plus Mini Kit (#74136: QIAGEN) was used in this study. RNA purification was performed by the method described in the kit, After RNA purification, the total RNA concentration was measured by using QIAxpert Instrument (QIAGEN). cDNA was synthesized using SuperScript® VILO™ cDNA. Synthesis Kit (#11754: Thermo Fisher Scientific). The synthesis of cDNA was performed by the method described in the kit. The synthesized cDNA was diluted 4 times with RNase free water, and the diluted cDNA solution was used as a sample Taqman Universal PCR Master Mix (#4304437: Thermo Fisher Scientific), Taqman® Gene Expression Assays, INVENTORIED (#4331182: Thermo Fisher Scientific), RNase free water, and the cDNA solution were mixed in amounts of 10 μl, 1 μl, 4 μl, and 5 μl, respectively, and the resulting mixture was used as a measurement sample solution. Quantitative polymerase chain reaction (qPCR) was conducted using ABI PRISM® 7900HT (Thermo Fisher Scientific) by a fluorescence probe method. Analysis was performed by SDS 2.4 (Thermo Fisher Scientific). The results were calculated by the percentage of the amount of ChAT mRNA expression levels in the compound administration group of Reference Example 1 increased from the amount of ChAT mRNA expression levels in the vehicle administration group to be 56.4% at 10 mg/kg.

Measurement of Acetylcholine (ACh) in Rat Cerebrospinal Fluid (CSF)
(1) Background Correlation between increase and decrease of intracerebral neurotransmitters and those in cerebrospinal fluid (CSF) was revealed by studies on rodents and the correlation was also seen in human (Lowe S et al. Psychopharmacology 219 (2012) 959-970). Thus, the changes in acetylcholine in CSF were measured in order to determine the changes in intracerebral acetylcholine by the test compounds.

(2) Compound Administration

In this study Fischer 344 male rats (Charles River Laboratories Japan, Inc.) with a body weight of about 150 to 250 g were used. The test compounds were orally administered to the rats once a day at 10 mg/kg for three days. The vehicle used was 0.01 mol/L hydrochloric acid.

(3) Sampling

At 24 hours after the administration of the vehicle and the test compounds, the CSF was collected from cisterna magna in a tube containing AchE inhibitors under pentobarbital anesthesia. The collected CSF was centrifuged at 3500×g at 4° C. for 10 minutes and the supernatant was collected. The collected supernatant was frozen with liquid nitrogen, and then stored at −80° C.

(4) Measurement of Ach by LC-MS

To 10 μL of the CSF was added 50 μL of acetylcholine-d9 chloride (ACh-d9) at a final concentration of 0.34 nmol/L as an internal standard. The mixture was pipetted and centrifuged at 1500×g at 4° C. for 10 minutes. The supernatant was collected and subjected to LC/MS (NexeraX2 (MS), TSQ Allis (HPLC)), and Ach was detected as precursor ion at m/z 146.050 and as product ion at m/z 87.071 and ACh-d9 as an internal standard was detected as precursor ion at m/z 155.088 and as product ion at m/z 87.000. The results were calculated by the percentage (% of control) of the ACh concentration in CSF in the compound administration group of Reference Example 1 increased from the ACh concentration in CSF in the vehicle administration group to be 156.8%.

Evaluation in Human Tau P301S Transgenic Mouse (1) Compound Administration

In this study, the test compounds were orally administered to human tau P301S transgenic mice once a day for three months from four-month-old to seven-month-old. The vehicle used was 0.01 mol/L hydrochloric acid.

(2) Sampling

At the initial day of the administration (four-month-old) and at the next day of the final administration, mice of vehicle administration group and test compound administration group were anesthetized under pentobarbital (50 mg/kg, i.p.) and perfused with PBS. After the perfusion, the forebrain including the medial septal area was collected and fixed with 4% parafomaldehyde.

(3) Preparation of Brain Coronal Frozen Section

The collected forebrain including the medial septal area was immersed and shaken overnight in 4% paraformaldehyde. The immersion solution was replaced with 7.5% sucrose solution. It was immersed and shaken overnight in 7.5% sucrose solution, and the immersion solution was replaced with 15% sucrose solution and it was immersed and shaken overnight. The immersion solution was replaced with 30% sucrose solution and it was immersed and shaken overnight. Brain coronal frozen sections with 30 μm thickness were prepared from the forebrain including the medial septal area by using a microtome (Leica, SM2000R).

(4) Immunohistochemistry of Choline Acetyltransferase (ChAT) Positive Cells

The prepared brain coronal frozen sections were stained with DAB (DAB PEROXIDASE SUBSTRATE KIT (Vector, SK-4100)) using a ChAT antibody (Santa Cruz, SC-20672) as a primary antibody. The section image including the medial septal area as shown in "The mouse Brain in stereotaxic coordinates" (COMPACT THIRD EDITION, Keith B. J. Franklin & George Paxinos) was taken by an all-in-one fluorescence microscope (KEYENCE, BL-X710) and ChM positive cells around the major axis of the medial septal area were counted by BZ analysis software (KEYENCE). The results were shown as a percentage of the number of ChAT positive cells in the vehicle administration group and the test compound administration group with respect to the number of ChAT positive cells at the time of initial administration (four-month-old). Data are expressed as the mean±SEM. The differences between the group at the time of initial administration and the vehicle-treated group (significant: *) was analyzed by an unpaired t-test, and also the differences between the vehicle-treated group and compound-treated group (significant: #) was analyzed by unpaired t-test. A value of P<0.05 was considered statistically significant. Statistical analyses were performed using the GraphPad Prism version 7.02. The results were shown in Table 1.

TABLE 1

| Treatment Group | Ratio (%) of number of ChAT positive cells compared to that in the initial administration |
|---|---|
| Group at the time of initial administration | 100.0 ± 4.5 |
| Vehicle administration group | 83.0 ± 5.8* |
| Reference Example 1 compound administration group (Dose: 5 mg/kg) | 105.3 ± 4.3# |

Neuroprotective and Restorative Effect on Cholinergic Neurons Using Fimbria-Formix Lesioned Rat Model (1) Preparation of Fimbria-Fornix Lesioned Rat Model In this studs Sprague-Dawley male rats (Charles River Laboratories Japan, Inc.) with a body weight of about 250 to 350 g were used. The rat was anesthetized under the combination of three drugs: midazolam (2 mg/kg s.c.), medetomidine hydrochloride (0.15 mg/kg s.c.) and butorphanol tartrate (2.5 mg/kg s.c.) and fixed with a brain stereotaxis apparatus (Narishige Co., Ltd.). The cranial was exposed and a hole with 5 mm width was drilled in the skull from the median line 2 mm posterior to Bregma. A razor with 4 mm width was pierced into the Bregma in 5.5 mm depth to cut fimbria-fornix. After hemostasis, the scalp was sutured. After the operation, the rat was brought back to the cage and recovered from the anesthesia. In the sham-operated group, a hole with 5 mm width was drilled in the skull from the median line 2 mm posterior to Bregma, but no razor was pierced, (2) Compound Administration The test compounds were orally administered to the rats once a day from five days to nine days after the operation (Example 1: 10 mg/kg) or from seven days to fourteen days after the operation (Example 3: 3 mg/kg). The vehicle used was 0.01 mol/L hydrochloric acid. In the sham-operated group, the vehicle was orally administered once a day similarly to the test compound administration group.

(3) Sampling

The rats were anesthetized under pentobarbital and transcardially perfused with ice-cold PBS. After the perfusion, the forebrain including the medial septal area was collected and immersed and shaken overnight with 4% paraformaldehyde. The immersion solution was replaced with 7.5% sucrose solution. It was immersed and shaken overnight in 7.5% sucrose solution, and the immersion solution was replaced with 15% sucrose solution and it was immersed and shaken overnight. The immersion solution was replaced with 30% sucrose solution and it was immersed and shaken overnight. Brain coronal frozen sections with 30 μm thickness were prepared from the forebrain including the medial septal area by using a microtome (Leica, SM2000R).

(4) Immunohistochemistry of Choline Acetyltransferase (ChAT) Positive Cells and Vesicular Acetylcholine Transporter (VAChT)

The prepared brain coronal frozen sections were stained with DAB (DAB PEROXIDASE SUBSTRATE KIT (Vector, SK-4100)) using a ChAT antibody (Santa Cruz, SC-20672) or a VAChT antibody (Merck Millipore, ABN100) as a primary antibody. The section image including the medial septal area or hippocampus as shown in "The mouse Brain in stereotaxic coordinates" (COMPACT THIRD EDITION, Keith B. J. Franklin & George Paxinos) was taken by an all-in-one fluorescence microscope (KEYENCE, BZ-X710) and ChAT positive cells of the medial septal area or optical density (OD) in hippocampal VAChT were measured by BZ analysis software (KEYENCE). The results were shown as a percentage of the number of ChAT positive cells of the medial septal area or OD in hippocampal VAChT in the vehicle administration group and the test compound administration group with respect to the number of ChAT positive cells of the medial septal area or OD in hippocampal VAChT in the sham-operated group. Data are expressed as the mean±SEM. The differences between the vehicle-treated group and compound-treated (significant: #) was analyzed by unpaired t-test. A value of P<0.05 was considered statistically significant. Statistical analyses were performed using the GraphPad Prism version 7.02. The results were shown in Tables 2 and 3.

TABLE 2

| Compound | Number of ChAT positive cells (%) at initial administration | Number of ChAT positive cells (%) in vehicle administration group | Number of ChAT positive cells (%) in test compound administration group |
|---|---|---|---|
| Reference Example 1 | 57.0 ± 7.5 | 38.4 ± 5.0 | 74.1 ± 9.3# |

TABLE 3

| Compound | OD in hippocampal VAChT (%) at initial administration | OD in hippocampal VAChT (%) in vehicle administration group | OD in hippocampal VAChT (%) in test compound administration group |
|---|---|---|---|
| Reference Example 1 | 51.7 ± 13.1 | 19.5 ± 6.4 | 66.1 ± 14.2# |

The invention claimed is:

1. A crystal of a monohydrochloride salt of 5,10-dimethyl-5,6,9,10,11,12-hexahydropyrido[4'',3'':4',5']thieno[2',3':4,5]pyrimido[1,2-a]thieno[3,2-f][1,4]diazepine-4,13-dione represented by formula (I):

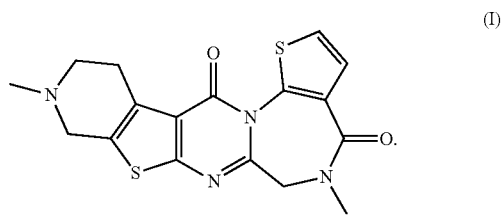 [SMILES: CN1CCc2c(sc3nc4n(c(=O)c23)-c2sccc2C(=O)N(C)C4)C1]

2. The crystal according to claim 1, which is an A-type crystal of 5,10-dimethyl-5,6,9,10,11,12-hexahydropyrido[4'',3'':4',5']thieno[2',3':4,5]pyrimido[1,2-a]thieno[3,2-f][1,4]diazepine-4,13-dione monohydrochloride salt represented by formula (I):

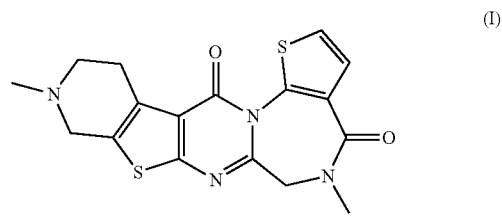 [SMILES: CN1CCc2c(sc3nc4n(c(=O)c23)-c2sccc2C(=O)N(C)C4)C1]

having diffraction peaks at diffraction angles (2θ±0.2°) of 11.6°, 20.8° and 25.7° in a powder X-ray diffraction using CuKα as an X-ray source.

3. The crystal according to claim 1, which is a B-type crystal of 5,10-dimethyl-5,6,9,10,11,12-hexahydropyrido[4'',3'':4',5']thieno[2',3':4,5]pyrimido[1,2-a]thieno[3,2-f][1,4]diazepine-4,13-dione monohydrochloride salt represented by formula (I):

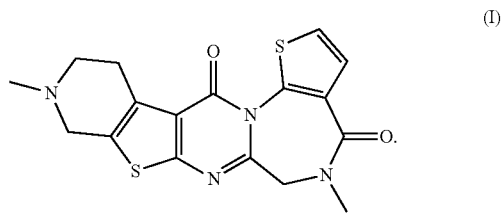 [SMILES: CN1CCc2c(sc3nc4n(c(=O)c23)-c2sccc2C(=O)N(C)C4)C1]

having diffraction peaks at diffraction angles (2θ±0.2°) of 9.7°, 10.1° and 17.9° in a powder X-ray diffraction using CuKα as an X-ray source.

4. The crystal according to claim 1, which is a C-type crystal of 5,10-dimethyl-5,6,9,10,11,12-hexahydropyrido[4'',3'':4',5']thieno[2',3':4,5]pyrimido[1,2-a]thieno[3,2-f][1,4]diazepine-4,13-dione monohydrochloride salt represented by formula (I):

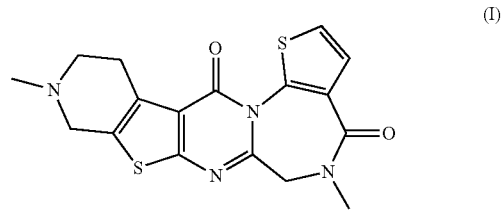 [SMILES: CN1CCc2c(sc3nc4n(c(=O)c23)-c2sccc2C(=O)N(C)C4)C1]

having diffraction peaks at diffraction angles (2θ±0.2°) of 6.0°, 7.7° and 16.9° in a powder X-ray diffraction using CuKα as an X-ray source.

5. The crystal according to claim 1, which is a D-type crystal of 5,10-dimethyl-5,6,9,10,11,12-hexahydropyrido[4″,3″:4′,5′]thieno[2′,3′:4,5]pyrimido[1,2-a]thieno[3,2-f][1,4]diazepine-4,13-dione monohydrochloride salt represented by formula (I):

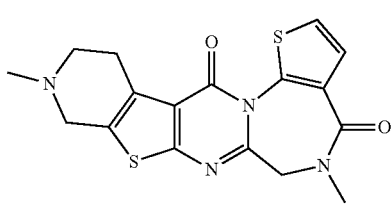

(I)

having diffraction peaks at diffraction angles (2θ±0.2°) of 6.6°, 14.6° and 26.4° in a powder X-ray diffraction using CuKα as an X-ray source.

6. The crystal according to claim 1, which is an E-type crystal of 5,10-dimethyl-5,6,9,10,11,12-hexahydropyrido[4″,3″:4′,5′]thieno[2′,3′:4,5]pyrimido[1,2-a]thieno[3,2-f][1,4]diazepine-4,13-dione monohydrochloride salt represented by formula (I):

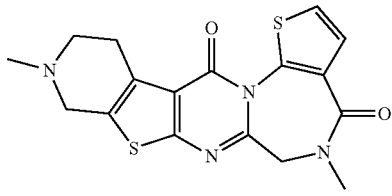

(I)

having diffraction peaks at diffraction angles (2θ±0.2°) of 6.4°, 11.3° and 27.3° in a powder X-ray diffraction using CuKα as an X-ray source.

7. The crystal according to claim 1, which is an F-type crystal of 5,10-dimethyl-5,6,9,10,11,12-hexahydropyrido[4″,3″:4′,5′]thieno[2′,3′:4,5]pyrimido[1,2-a]thieno[3,2-f][1,4]diazepine-4,13-dione monohydrochloride salt represented by formula (I):

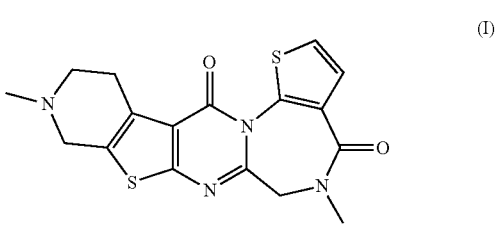 [SMILES: CN1CCc2c(sc3nc4n(c(=O)c23)-c2sccc2C(=O)N(C)C4)C1]

(I)

having diffraction peaks at diffraction angles (2θ±0.2°) of 7.3°, 9.3° and 10.7° in a powder X-ray diffraction using CuKα as an X-ray source.

8. A pharmaceutical composition comprising the crystal according to claim 1.

9. A method of treating Alzheimer's disease, comprising administering the crystal according to claim 1 to a patient in need thereof.

10. A method of treating Dementia with Lewy bodies, comprising administering the crystal according to claim 1 to a patient in need thereof.

11. A method of treating Parkinson disease with dementia, comprising administering the crystal according to claim 1 to a patient in need thereof.

* * * * *